United States Patent [19]
Sholder

[11] Patent Number: 5,741,308
[45] Date of Patent: *Apr. 21, 1998

[54] DUAL-CHAMBER IMPLANTABLE PACEMAKER AND METHOD OF OPERATING SAME FOR AUTOMATICALLY SETTING THE PACEMAKER'S AV INTERVAL AS A FUNCTION OF A NATURAL MEASURED CONDUCTION TIME

[75] Inventor: Jason A. Sholder, Beverly Hills, Calif.

[73] Assignee: Pacesetter, Inc., Sylmar, Calif.

[*] Notice: The term of this patent shall not extend beyond the expiration date of Pat. No. 5,334,220.

[21] Appl. No.: 440,599

[22] Filed: May 15, 1995

Related U.S. Application Data

[63] Continuation-in-part of Ser. No. 225,226, Apr. 8, 1994, abandoned, which is a continuation-in-part of Ser. No. 219,065, Mar. 29, 1994, abandoned, which is a continuation-in-part of Ser. No. 976,153, Nov. 13, 1992, Pat. No. 5,334,220.

[51] Int. Cl.[6] ..................................... A61N 1/365
[52] U.S. Cl. ........................................... 607/9
[58] Field of Search ............................. 607/9, 14

[56] References Cited

U.S. PATENT DOCUMENTS

| | | | |
|---|---|---|---|
| 4,343,311 | 8/1982 | Markowitz | 607/9 |
| 4,378,020 | 3/1983 | Nappholz et al. | 607/9 |
| 4,386,610 | 6/1983 | Leckrone | 607/9 |
| 4,397,316 | 8/1983 | Barthel | 607/9 |
| 4,412,541 | 11/1983 | Schaldach et al. | 607/9 |
| 4,429,697 | 2/1984 | Nappholz et al. | 128/419 |
| 4,523,593 | 6/1985 | Rueter | 607/9 |
| 4,554,921 | 11/1985 | Boute et al. | 128/419 |
| 4,712,555 | 12/1987 | Thornander et al. | 128/419 |
| 4,722,341 | 2/1988 | Hedberg et al. | 128/419 |
| 4,788,980 | 12/1988 | Mann et al. | 128/419 |
| 4,847,617 | 7/1989 | Silvian | 340/870 |
| 4,940,052 | 7/1990 | Mann et al. | 128/419 |
| 4,944,298 | 7/1990 | Sholder | 128/419 |
| 4,967,746 | 11/1990 | Vandegriff | 607/9 |
| 4,974,589 | 12/1990 | Sholder | 128/419 |
| 5,086,774 | 2/1992 | Duncan | 128/419 |
| 5,144,950 | 9/1992 | Stoop, et al. | 128/419 |
| 5,179,949 | 1/1993 | Chirife | 607/9 |
| 5,334,220 | 8/1994 | Sholder . | |
| 5,340,361 | 8/1994 | Sholder . | |

*Primary Examiner*—William E. Kamm

[57] ABSTRACT

A dual-chamber implantable pacemaker automatically sets its AV or PV interval to a value that is a function of the measured natural conduction time, or AR interval, of a user of the pacemaker. The AR interval is determined on a regular basis, thereby permitting the AV or PV interval set by the pacemaker to adaptively change with any changes in the AR interval. The AV or PV interval is set to a value that is a prescribed amount Δ less than or greater than the measured AR interval. The measured AR interval is typically averaged, or otherwise determined or estimated, based on measurements of several cardiac cycles.

16 Claims, 11 Drawing Sheets

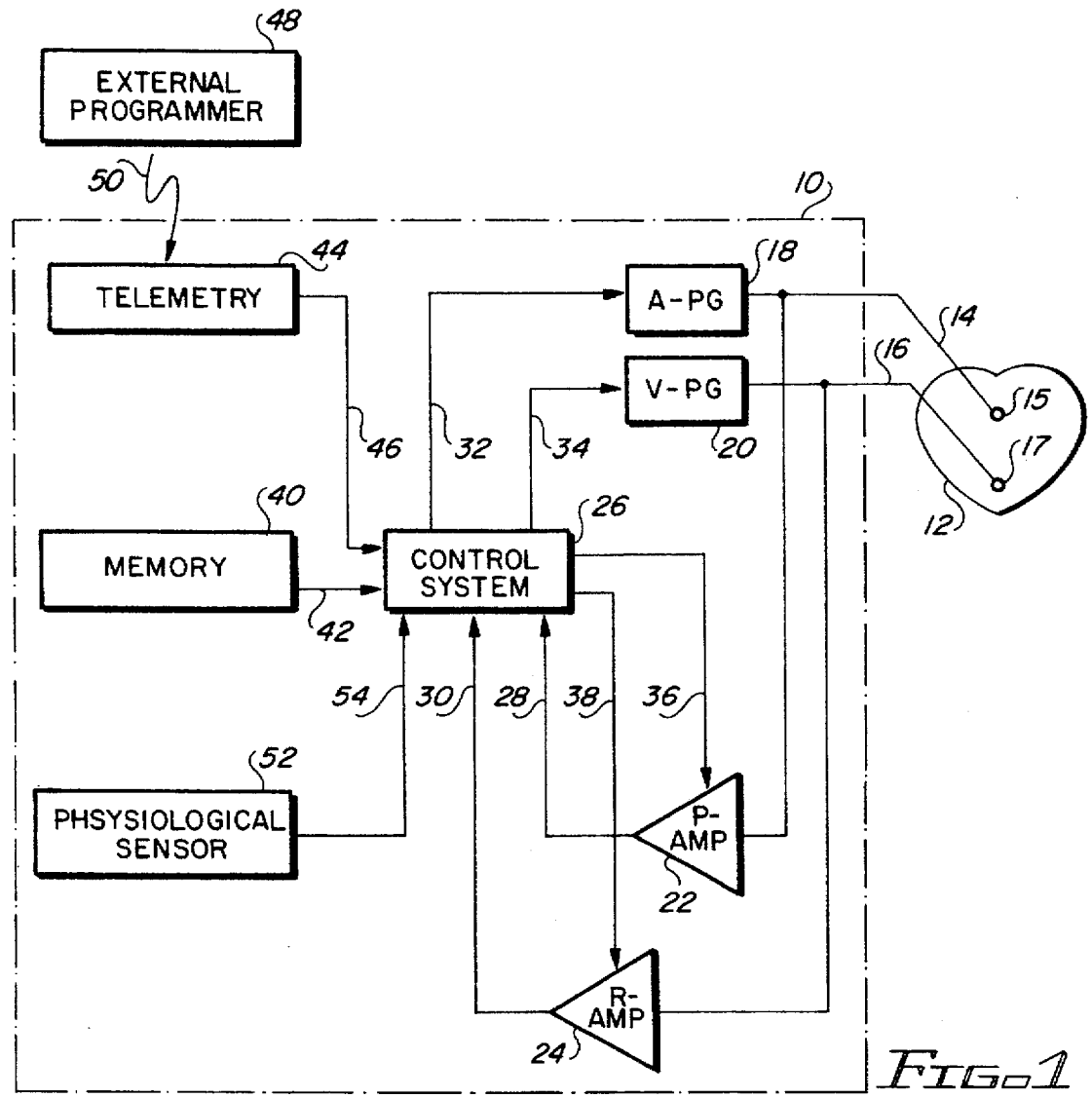
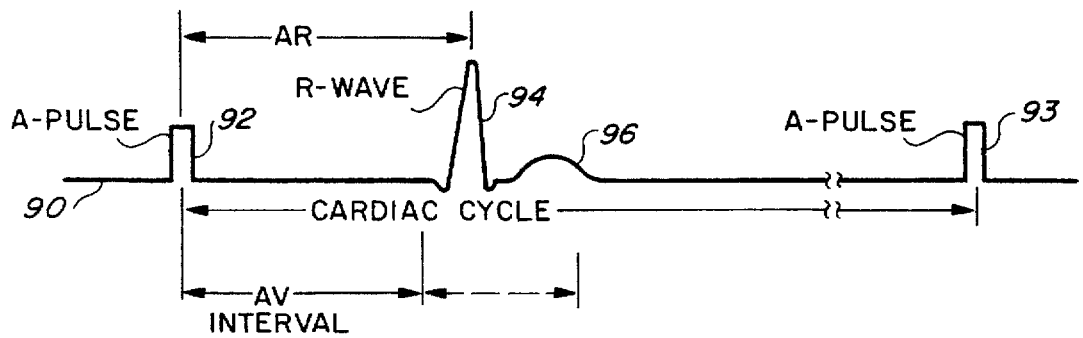

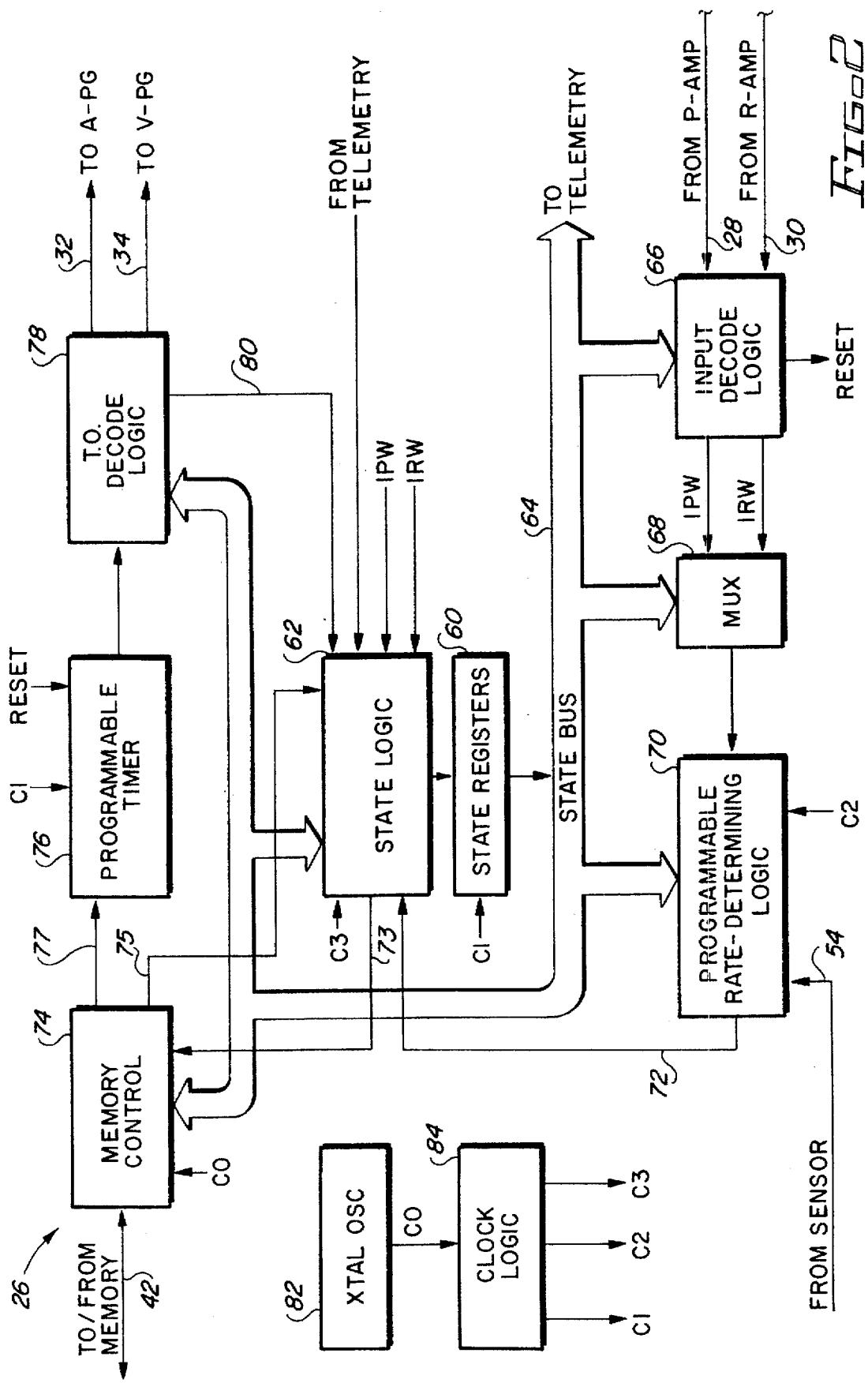

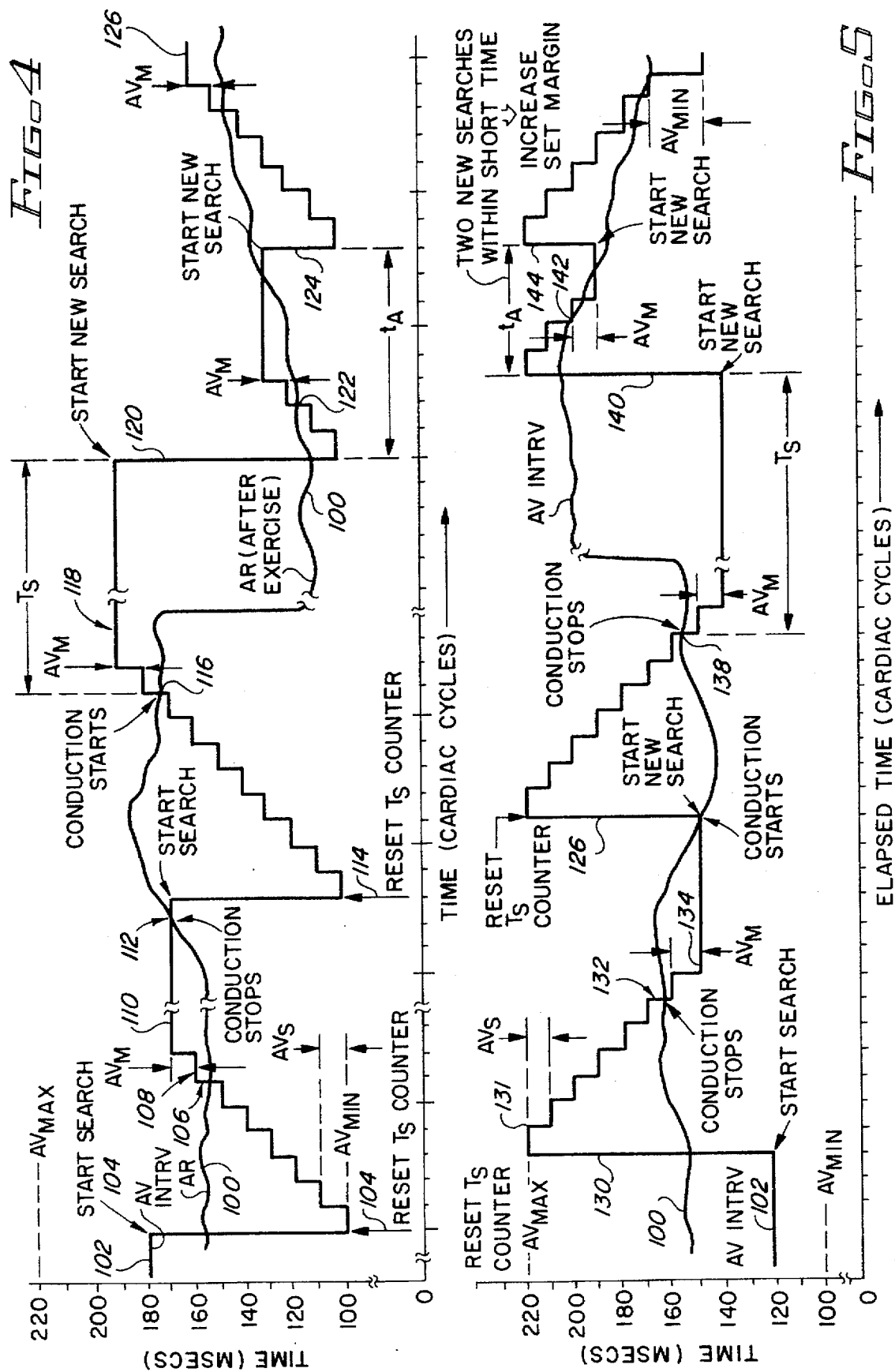

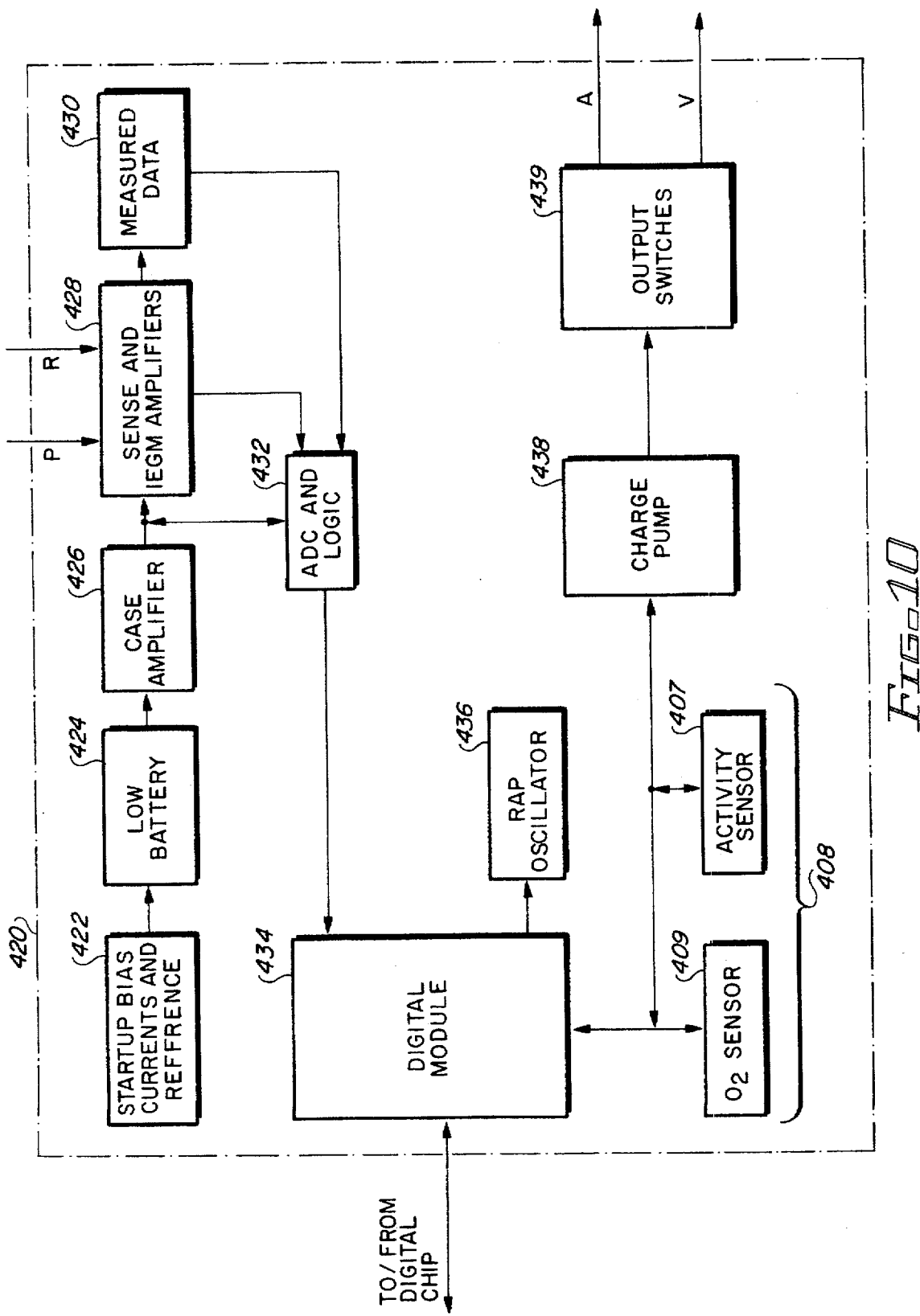

5,741,308

DUAL-CHAMBER IMPLANTABLE PACEMAKER AND METHOD OF OPERATING SAME FOR AUTOMATICALLY SETTING THE PACEMAKER'S AV INTERVAL AS A FUNCTION OF A NATURAL MEASURED CONDUCTION TIME

This application is a continuation-in-part of application Ser. No. 08/225,226, filed Apr. 8, 1994, now abandoned, which application is a continuation-in-part of application Ser. No. 08/219,065, filed Mar. 29, 1994, now abandoned; which is a continuation-in-part of application Ser. No. 07/976,153, filed Nov. 13, 1992, now U.S. Pat. No. 5,334,220 which applications are incorporated herein by reference.

FIELD OF THE INVENTION

The present invention relates to implantable medical devices and methods, and more particularly, to an implantable dual-chamber pacemaker that automatically sets its atrioventricular (AV) delay, or AV interval, to a value that is a prescribed amount less than or greater than a measured natural conduction time of a patient within whom the pacemaker is implanted.

BACKGROUND OF THE INVENTION

The heart is a pump that pumps life-sustaining blood throughout the body of the patient. The human heart comprises a left side and a right side with each side having a first chamber known as the atrium, and a second chamber known as the ventricle. The atrium receives blood returning from other body locations. At an appropriate time, determined by the sinoatrial (SA) node, an electrical stimulus is provided that causes the muscle tissue surrounding the atrium to depolarize. Depolarization of the atrial muscle tissue is manifest by the occurrence of an electrical signal known as the P-wave. Immediately following the P-wave, the atrial muscle tissue physically contracts, forcing the blood held in the atrium through a one-way valve into the ventricle. The SA node stimulus that caused the atrium to depolarize also travels to the ventricle through the atrioventricular (AV) node and the atrioventricular (AV) bundle, also known as the Bundle of His. The AV node is a mass of neuromuscular heart tissue situated in the lower middle part of the right atrium. It receives the impulse to contract from the sinoatrial node, via the atria, and transmits it through the Bundle of His to the ventricles. The Bundle of His is composed of neuromuscular heart fibers (Purkinje fibers) that pass from the AV node forward to the septum between the ventricles, where it divides into right and left bundle branches, one for each ventricle. The fibers thus transmit the SA node stimulus from the atria, via the AV node, to the ventricles. However, as the SA node stimulus travels through the AV bundle, it is delayed by an amount commensurate with the same time it should take the blood to physically flow from the atrium to the ventricle.

After the delay through the AV node, which delay is referred to herein as the "natural conduction time" of the heart, the SA node stimulus arrives at the ventricular muscle tissue, causing it to depolarize. Depolarization of the ventricular muscle tissue is manifest by the occurrence of an electrical signal known as the R-wave (sometimes referred to as the QRS complex). Immediately following the R-wave, the ventricular muscle tissue physically or mechanically contracts, forcing the blood held therein through one or more arteries to various body locations. In this manner, then, the heart "beats" or pumps blood by having the atria contract at a rate determined by the SA node, and after the natural conduction time, by having the ventricles contract. After a period of time, when the atrium has refilled with blood returning from throughout the body, the process repeats.

The heart of a typical healthy patient may beat 60–70 times per minute when the patient is at rest. When the patient is undergoing significant physiological stress, as occurs, e.g., during physical exercise, the rate at which the heartbeats, the "heart rate," increases significantly, e.g., up to 150–170 times per minute. The above-described process wherein the atria and ventricles sequentially depolarize and contract in order to pump blood and get ready to depolarize again, is referred to herein as the "cardiac cycle." A given cardiac cycle thus includes one R-wave (or equivalent ventricular activity evidencing depolarization of the ventricles) and one P-wave (or equivalent atrial activity evidencing depolarization of the atria). The length of the cardiac cycle (which represents the period of the heart rate) may be measured as the time interval between successive P-waves or R-waves, although R-waves are usually used because they are easier to identify on an ECG.

A pacemaker is an implantable medical device that monitors the activity of the heart for the occurrence of P-waves and/or R-waves, and steps in with electronically generated stimuli, when needed, to force the depolarization of the atria and/or ventricles. A pacemaker-generated stimulus that is delivered to the atrium is referred to herein as an "A-pulse." A pacemaker-generated stimulus that is delivered to the ventricle is referred to herein as a "V-pulse." Most pacemakers are configured to provide an A-pulse and/or V-pulse only if a prescribed period of time has elapsed without the occurrence of a P-wave and/or an R-wave, i.e., without the occurrence of natural heartbeats.

The prescribed period of time used by the pacemaker between contraction of the ventricle and contraction of the atrium is generally referred to as the V-A Interval, or the atrial escape interval. For most dual-chamber pacemaker modes of operation, only if a P-wave does not occur during the atrial escape interval will the pacemaker step in at the conclusion of such interval and generate an A-pulse.

The prescribed period of time used by the pacemaker between contraction of the atrium and contraction of the ventricle is referred to as the "PR interval," or sometimes it is called the "AV Delay." The pacemaker, for most dual-chamber modes of operation, generates a V-pulse only if the PR Interval elapses after atrial activity without the occurrence of an R-wave.

In the above-described manner, the heart is thus afforded as much time as possible to beat on its own before the electronically-generated stimuli of the pacemaker are delivered to the heart, causing it to beat at the rate set by the pacemaker.

When a pacemaker is first implanted in a patient, or thereafter, the value of the AV interval is set by an attending physician or cardiologist to a value that is selected to optimally assist the patient's heart as it performs its critical function of a pump. For many patients, such AV interval value is a value that is somewhat longer than the natural conduction time of the heart, thereby affording the patient's heart as long a time period as possible before stepping in with the pacemaker generated stimulation pulse (V-pulse). Such action further serves to lengthen the battery life of the pacemaker, because it reduces the number of stimulation pulses that the pacemaker generates, and thereby conserves the limited energy available in the pacemaker battery. However, for other patients, it may be desirable to set the AV interval value at a value that is less than the natural conduction time of the heart, thereby assuring that a V-pulse is preemptively generated with most every cardiac cycle. See, e.g., Applicant's copending application, entitled IMPLANTABLE PACEMAKER HAVING ADAPTIVE AV INTERVAL FOR PROVIDING VENTRICULAR PACING, Ser. No. 07/975,747, filed Nov. 13, 1992, now U.S. Pat. No. 5,340,361 is incorporated herein by reference.

Unfortunately, while the AV interval of a pacemaker can be programmably set to a desired value, the natural conduction time of the patient may vary, either with time, or with the medical or physiological condition of the patient. For example, the natural conduction time may vary as a function of whether the patient is undergoing physiological stress (e.g., exercise), or whether the patient is under the influence of medication. In most instances, it would be desirable to have the AV interval closely mimic the natural conduction time, because such natural conduction time normally represents the optimum timing between depolarization of the atria and depolarization of the ventricles. However, when the natural conduction time is varying, it is not possible for the AV interval of the pacemaker to mimic such time. What is needed, therefore, is an implantable pacemaker that automatically adjusts or sets its AV interval to a value that tracks or mimics changes in the natural conduction time.

It is significant to note that the AV interval should not be set to the same value as the natural conduction time, else the V-pulse will be generated at the same time that the R-wave occurs, a condition known as "fusion." Fusion is not necessarily harmful to the heart, but it represents the expenditure of wasted energy, as the cardiac tissue is not capable of responding to the V-pulse stimulus when it is refractory. The cardiac tissue is refractory concurrent with and/or immediately following depolarization, and remains refractory until the occurrence of the T-wave. Thus, in order to conserve the limited energy of the pacemaker, it is important that fusion be avoided, and that the V-pulse not be applied to the cardiac tissue concurrent with and/or immediately following the occurrence of an R-wave. However, if the natural conduction time varies, as it does, it is quite probable that the natural conduction time will wander into the AV interval time, causing fusion to occur. Thus, what is needed is not only an implantable pacemaker that automatically adjusts its AV interval to track or mimic the natural conduction time, but that also adjusts the AV interval to a value that is close to, but not the same as, the natural conduction time, thereby providing the desired tracking while avoiding fusion with the natural depolarization of the patient's heart.

SUMMARY OF THE INVENTION

The present invention addresses the above and other needs by providing a dual-chamber implantable pacemaker that automatically sets its AV (or PV) interval to a value that is a function of the measured natural conduction time, or AR interval, of a user of the pacemaker. Typically, the AV (or PV) interval is automatically set to a value that is equal to the measured AR interval $\pm \Delta$, where $\Delta$ is a programmable amount, e.g., 1 to 100 msec. In this manner, any ventricular stimulation pulses (V-pulses) generated by the pacemaker at the conclusion of the pacemaker-defined AV interval (or PV interval, in those instances where a natural atrial event, or P-wave, occurs during the cardiac cycle instead of a stimulated atrial event, or A-pulse) occur at a time in the cardiac cycle that avoids fusion with the natural ventricular depolarization of a patient's heart.

As indicated above, a natural ventricular depolarization occurs at the conclusion of the natural conduction time of the heart, and is manifest by the occurrence of an R-wave. The natural conduction time comprises that time interval from the onset of atrial activity to the depolarization of the ventricular muscle tissue, i.e., to the occurrence of an R-wave. The present invention thus sets the time when the V-pulse occurs within the cardiac cycle so that it occurs near the same time as an R-wave would occur, but does not occur at the same time as an R-wave. Rather, the V-pulse is set to occur at a time within the cardiac cycle that is $\pm \Delta$ from when the R-wave would occur.

In accordance with one aspect of the invention, then, the AV interval of the pacemaker is automatically set by the pacemaker to a value that is $\pm \Delta$ of the measured natural conduction time. The natural conduction time, in turn, is measured either by simply noting, or logging, the time interval between an atrial event and an R-wave during a normal cardiac cycle (if an R-wave is sensed during the cardiac cycle); or (if an R-wave is not sensed during the cardiac cycle) by extending the AV interval of a subsequent cardiac cycle by an amount sufficient to permit the occurrence of an R-wave, and noting the time interval from the atrial event of that cardiac cycle to the R-wave that is allowed to occur. Hence, the present invention advantageously sets the AV interval to track or follow changes that may occur in the natural conduction time.

In accordance with another aspect of the invention, the natural conduction time, or AR interval, may be determined or measured over several cardiac cycles, e.g., averaged over several cardiac cycles, so that the AV (or PV) interval is not set to an erroneous value that is based on a single AR interval measurement that is not representative of the correct natural conduction time.

In accordance with still a further aspect of the invention, the VA interval of the pacemaker is changed by an appropriate amount $\Delta 2$ to compensate for changes of $\Delta 1$ made to the AV interval, so that the overall pacing cycle length, referred to as the A-to-A interval, is not altered.

One embodiment of the invention may be characterized as a method of operating a dual-chamber implantable pacemaker. Such pacemaker has an AV (or PV) interval (AV/PV interval) that defines the maximum time permitted by the pacemaker after atrial activity before a ventricular stimulation pulse (V-pulse) is generated. The method includes: (a) measuring a PR/AR interval as the time interval between atrial activity and a natural ventricular depolarization (R-wave), where atrial activity comprises either a natural atrial depolarization (P-wave) or an atrial stimulation pulse (A-pulse), whichever occurs first in a given cardiac cycle; and (b) setting the AV/PV interval of the pacemaker to be equal to the measured PR/AR interval $\pm \Delta$, where $\Delta$ is a time increment ranging from, e.g., 1 to 100 msec, so that the PV/AV interval of the pacemaker tracks the measured PR/AR interval within $\pm \Delta$.

Another embodiment of the invention may be viewed as a method of stimulating cardiac tissue using an implanted dual-chamber pacemaker. The pacemaker has means for sensing atrial and ventricular events, and means for generating a ventricular stimulation pulse (V-pulse) and delivering the V-pulse to a prescribed ventricular location. The method includes: (a) determining a natural conduction time of the cardiac tissue as the difference between an atrial event and a natural ventricular event within a given cardiac cycle associated with the cardiac tissue; and (b) generating and delivering the V-pulse to the prescribed ventricular location at a time following an atrial event in each cardiac cycle that is a prescribed amount different from the natural conduction time determined in step (a). In this manner, the natural conduction time determines when the V-pulse is generated within the given cardiac cycle.

The invention also may be characterized as a dual-chamber pacemaker that controls ventricular pacing as a function of a natural conduction time of a patient's heart. Such pacemaker includes an atrial channel and a ventricular channel, each adapted to be coupled to the patient's heart. Also included in the pacemaker is a means for sensing a natural conduction time interval of the patient's heart through the atrial and ventricular channels, where the natural conduction time interval comprises the time interval within a given cardiac cycle that commences with atrial activity, whether sensed or paced, and terminates upon a natural ventricular depolarization (R-wave). Further included in the pacemaker is a pulse generator that generates a ventricular stimulation pulse (V-pulse) in the ventricular channel at a prescribed time within the cardiac cycle that is a function of the natural conduction time interval.

It is thus a feature of the present invention to provide an implantable pacemaker that automatically sets its AV interval to a value that is just less than, or just greater than, the natural conduction time of a patient's heart, thereby mimicking insofar as possible the natural timing associated with the heart.

It is another feature of the invention to provide such setting of the AV interval while avoiding fusion, i.e., preventing the issuance of a V-pulse on top of an R-wave, thereby assuring that any V-pulses that are issued are effective at depolarizing the ventricular muscle tissue.

It is yet another feature of the invention to provide an automatic AV setting procedure that is automatically invoked, e.g., every cardiac cycle or whenever an R-wave is sensed; or in accordance with a prescribed schedule, e.g., every x cardiac cycles, where x is an integer greater than ten.

It is still another feature of the invention to provide a dual-chamber pacemaker, and method of operating such pacemaker, wherein the overall A-to-A interval of the pacemaker remains unchanged even though the AV interval does change with variations in the natural conduction time.

BRIEF DESCRIPTION OF THE DRAWINGS

The above and other aspects, features and advantages of the present invention will become more apparent from the Detailed Description of the Invention, presented in conjunction with the following drawings, wherein:

FIG. 1 is a functional block diagram of a dual-chamber programmable pacemaker;

FIG. 2 is a block diagram of one embodiment of the control logic of the pacemaker of FIG. 1;

FIG. 3 diagrammatically illustrates a cardiac cycle and illustrates the manner in which the PV (or AV) interval is adjusted to avoid fusion;

FIG. 4 is a diagram illustrating how the present invention adaptively adjusts the PV (or AV) interval over several cardiac cycles in order to incrementally increase such interval from a minimum value to a value that is greater than the natural conduction time, thereby avoiding fusion;

FIG. 5 is a diagram as in FIG. 4, except that the PV (or AV) interval is incrementally decreased over several cardiac cycles from a maximum value to a value that is less than the natural conduction time, thereby avoiding fusion;

FIG. 10 is a block diagram of the analog chip portion of the pacemaker of FIG. 9;

Corresponding reference characters indicate corresponding components throughout the several views of the drawings.

DETAILED DESCRIPTION OF THE INVENTION

Figure 6:
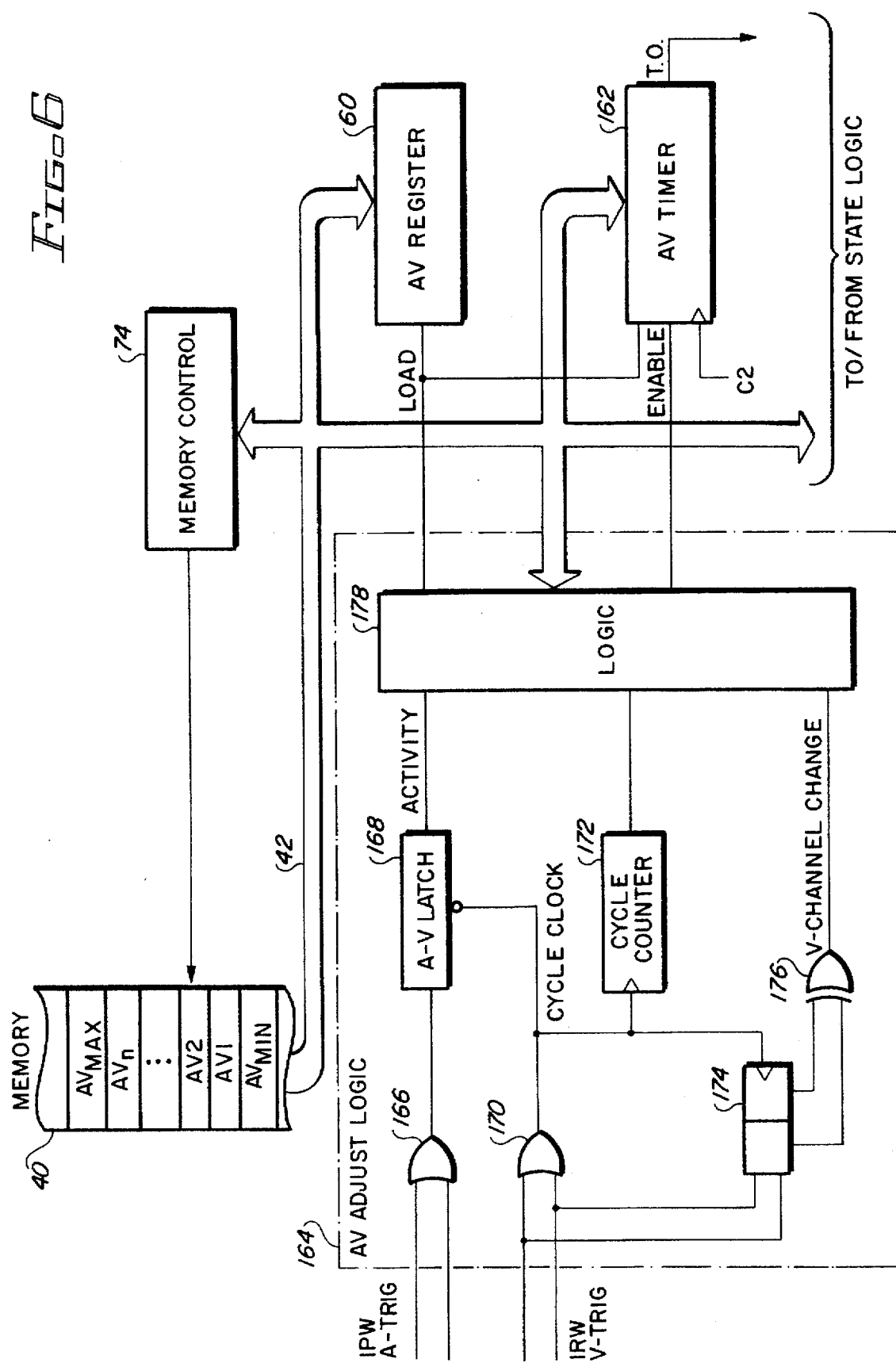
FIG. 6 is a functional block diagram of a portion of the control system of a pacemaker used to carry out an AV interval adjustment of the present invention.

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to an implantable dual-chamber pacemaker, and a method of operating an implantable dual-chamber pacemaker, that automatically sets or adjusts the AV interval (or PV interval) of the pacemaker to a value that is equal to the natural conduction time of the patient, plus or minus (±Δ) a prescribed amount, Δ, thereby avoiding fusion. Automatic setting of the AV (or PV) interval is desirable, for example, in order to allow the patient's heart a longer time to beat on its own, even when changes occur in the natural conduction time of a patient. Alternatively, automatic adjustment of the PV (or AV) interval may be desirable in patients suffering from certain cardiac conditions, such as a cardiomyopathy, as disclosed in Applicant's U.S. Pat. No. 5,340,361, entitled, IMPLANTABLE PACEMAKER HAVING ADAPTIVE AV INTERVAL FOR PROVIDING VENTRICULAR PACING, previously cited and incorporated herein by reference.

Throughout the discussion that follows, reference will frequently be made to the AV interval. It is to be understood that all such references to the AV interval also apply to the PV interval, and that whether the AV or PV interval is used depends upon the particular type of atrial activity—an A-pulse or a P-wave—that starts the AV (or PV) interval. Similarly, it is to be understood that any references made to the PV interval also apply to the AV interval. It is further to be understood that when the PV interval is used, it will typically be (but does not have to be) shorter than the AV interval by a prescribed amount, e.g., 20–40 msec, to account for the latency time involved between applying an A-pulse and having the atrial tissue respond with a depolarization. Those of skill in the art can readily fashion appropriate circuitry to utilize either an AV interval or a PV interval, whichever applies to a given cardiac cycle. For the discussion that follows, then, where reference is made to the AV interval, such AV interval should be considered as the time interval between atrial channel activity, whether such atrial channel activity comprises an A-pulse or a P-wave, and the subsequent delivery of a ventricular stimulation pulse (V-pulse).

Advantageously, the present invention may be implemented using a wide variety of dual-chamber pacemaker configurations and pacemaker hardware. Any pacemaker configuration that allows the pacemaker AV (or PV) interval to be automatically set to a desired value may be used to implement the invention. The descriptions that follow are only exemplary of a few of such configurations.

Reference will first be made to FIG. 1, where a functional block diagram of a dual-chamber pacemaker 10 is illustrated. Such functional diagram will be used to initially teach the primary functions carried out by the pacemaker 10. Various embodiments of the actual hardware and components used within the pacemaker 10 to carry out the pacemaker functions will then be described in conjunction with FIGS. 9–11 and 2 and 6. Next, techniques or methods that may be used by the pacemaker 10 to implement the present invention will be described in conjunction with the flow diagrams and timing diagrams of FIGS. 12, 13, 3–5, 7 and 8-1 and 8-2.

Referring then to FIG. 1, the pacemaker 10 is coupled to a heart 12 by way of leads 14 and 16. (Note, in subsequent figures, e.g., FIG. 9, the leads 14 and 16 are referred to as the lead system 19.) The lead 14 has an electrode 15 that is in contact with one of the atria of the heart, and the lead 16 has an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual-chamber pacer 10 is a control circuit or control system 26. The control system 26 receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control circuit or system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. A stimulation pulse generated by the A-PG 18 is referred to as the "A-pulse," and the stimulation pulse generated by the V-PG 20 is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large A-pulse or V-pulse, respectively, that is present at the input terminals of such amplifiers during this time. Such blanking action also helps prevent residual electrical signals present in the muscle tissue as a result of the pacer stimulation from being interpreted as P-waves or R-waves.

Still referring to FIG. 1, the pacer 10 also includes a memory circuit 40 that is coupled to the control system 26 over a suitable data/address bus 42. The memory circuit 40 allows certain control parameters, used by the control system 26 in controlling the operation of the pacemaker, to be programmably stored and modified, as required, in order to customize the pacer's operation to suit the needs of a particular patient. Such data includes the basic timing intervals used during operation of the pacemaker, such as the programmed atrial escape interval (AEI). For purposes of the present invention, such data may also include a family of AV interval data that may be retrieved during an adjustment sequence of the AV interval, as explained more fully below. Further, data sensed during the operation of the pacer may be stored in the memory 40 for later retrieval and analysis.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be any suitable electromagnetic link, such as an RF (radio frequency) channel. Advantageously, through the external programmer 48 and the communication link 50, desired commands may be sent to the control system 26. Similarly, through this communication link 50 and the programmer 48, data (either held within the control system 26, as in a data latch, or stored within the memory 40), may be remotely received from the pacer 10. In this manner, noninvasive communications can be established from time to time with the implanted pacer 10 from a remote, non-implanted location. Many suitable telemetry circuits known in the art that may be used with the present invention for the telemetry circuit 44. See, e.g., U.S. Pat. No. 4,847,617, incorporated herein by reference.

The pacer 10 in FIG. 1 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the V-pulse generator 20, and corresponding portions of the control system 26, are commonly referred to as the ventricular channel. Throughout the discussion that follows, frequent reference will be made to "atrial channel activity" or "ventricular channel activity." Atrial channel activity thus comprises either the sensing of a P-wave by the sense amplifier 22, or the generating of an A-pulse by the A-pulse generator 18. Similarly, ventricular channel activity comprises either the sensing of an R-wave by the sense amplifier 24 or the generation of a V-pulse by the V-pulse generator 20.

In some pacemakers that implement the present invention, the pacemaker 10 may further include one or more physiological sensors 52 that is/are connected to the control system 26 of the pacer over a suitable connection line 54. While the sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of physiologic sensors, such as sensors that sense the oxygen content of blood, respiration rate, pH of blood, body motion, and the like, may also be used in lieu of, or in addition to, an activity sensor. The type of sensor, if any, used is not critical to the present invention. Any sensor or combination of sensors capable of sensing some physiological parameter relatable to the rate at which the heart should be beating can be used. A pacemaker using such sensors is commonly referred to as a "rate-responsive" pacemaker because such a pacemaker adjusts the rate (escape interval) of the pacer in a manner that tracks the physiological needs of the patient.

Figure 9:
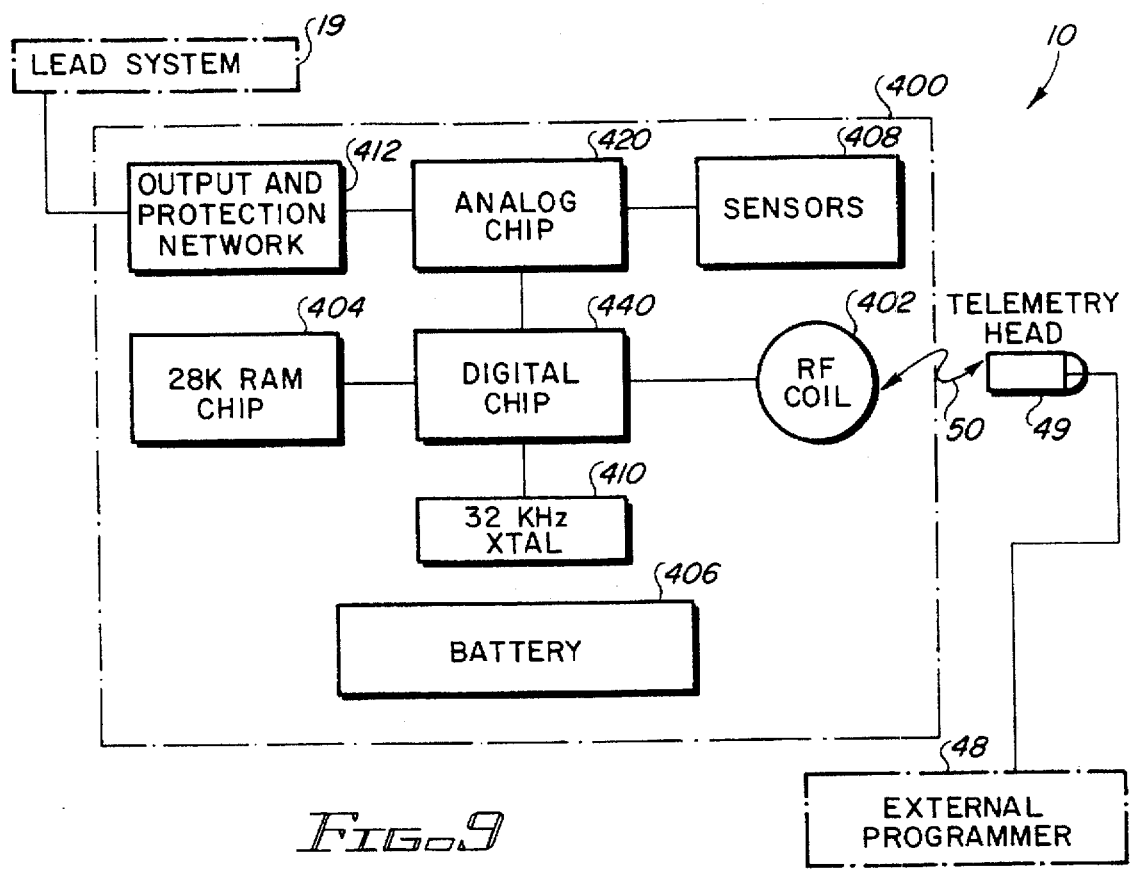
FIG. 9 is a block diagram of a pacing system that depicts, in accordance with a preferred embodiment of the invention, the main hardware components of an implantable pacemaker.

Referring next to FIG. 9, there is shown a preferred configuration of a pacing system made in accordance with the present invention. The system includes the external programmer 48, the implantable pacemaker 10, and the lead system 19. The lead system 19 includes conventional atrial and ventricular leads and electrodes, as described previously. The lead system 19 may also include an oxygen sensor lead, which lead contains an LED-detector assembly used to measure the oxygen content of the blood. Such a lead is described, e.g., in U.S. Pat. No. 4,815,469, incorporated herein by reference.

The external programmer 48 includes a telemetry head 49 that is positioned proximate the implantable pacemaker 10 whenever the communication link 50 is to be established between the pacemaker 10 and the external programmer 48. The external programmer may be of conventional design, as described, e.g., in U.S. Pat. No. 4,809,697, incorporated herein by reference.

The components of the pacemaker 10 are housed within a suitable sealed case or housing 400 (which case or housing is represented in FIG. 9 by the dashed line 400). The case 400 is preferably a titanium metal case. The components within the case 400 include an RF coil 402, a memory chip 404, a battery 406, one or more sensors in a sensor circuit 408, a crystal 410, an output/protection network 412, an analog chip 420 and a digital chip 440.

The battery 406, which is by volume the largest component within the pacemaker 10, may be of conventional design, and is a lithium battery that provides operating power to all of the electronic circuits within the pacemaker. The RF coil 402 is used to establish the communication link 50 with the telemetry head 49. The crystal 410 is used in conjunction with a crystal oscillator circuit on the digital chip 440 (described below) to provide a stable clock frequency for the pacemaker circuits. In the preferred embodiment, the frequency of the crystal oscillator is 32 KHz, although any suitable frequency could be used. The sensor circuit 408 includes appropriate sensors used by the pacemaker as it carries out a rate-responsive pacing function. For example, in one embodiment, the sensor circuit 408 includes an accelerometer adapted to sense patient activity.

The memory chip 404 is a low-power static random access memory (RAM) chip wherein the operating parameters, e.g., control variables, of the pacemaker may be stored, and wherein sensed data may be stored, as required. The analog chip 420 and the digital chip 440 contain the main processing and control circuits of the pacemaker. These chips are advantageously designed to minimize the number of components needed external thereto for operation of the pacemaker. The analog chip 420 interfaces with the lead system 19 through the output and protection network 412, which network includes output capacitors, appropriate feed-through connectors to allow electrical connection through the hermetically sealed case, and the like, as are commonly used in implantable medical devices.

Referring next to FIG. 10, a block diagram of the analog chip 420 is shown. The analog chip contains all the necessary sub-systems and modules to interface to the lead system 19 and the digital chip 440. For example, a startup/bias-current/reference module 422 contains the power-up signals used to initialize the pacer circuit when the battery is first applied. A low battery module 424 detects four voltage levels of the battery voltage for determining the battery status. A case amplifier 426 generates a CASE bias voltage that is used as a reference for the sense and IEGM (intracardiac electrogram) amplifier module 428. The module 428 includes the P-wave amplifier 22 and the R-wave amplifier 24, described above in FIG. 1. A measured data module 430 measures the battery voltage and current and other analog parameters of the pacing system. An ADC and Logic module 432 includes an analog-to-digital converter (ADC) and timing logic that are used to convert the analog signals of the pacemaker to 8-bit digital words. These digital words are then passed to a digital module 434, which module is used to generate all the basic timing and bus control functions as data is passed back and forth between the analog chip 420 and the digital chip 440.

Still referring to FIG. 10, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor network 408. The sensor network 408 includes appropriate sensors for sensing activity and other parameters. For example, an O2 sensor circuit 409 may be used in conjunction with the oxygen sensor lead, when used, to measure blood oxygen of the patient. An activity sensor 408 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the output leads at the appropriate time to form the appropriate stimulation pulses.

It is thus seen that the analog chip 420 contains the necessary circuitry to sense and detect atrial or ventricular events, digitize IEGM waveforms, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The condition of the battery is monitored, and independent Runaway Protection is provided.

Figure 11:
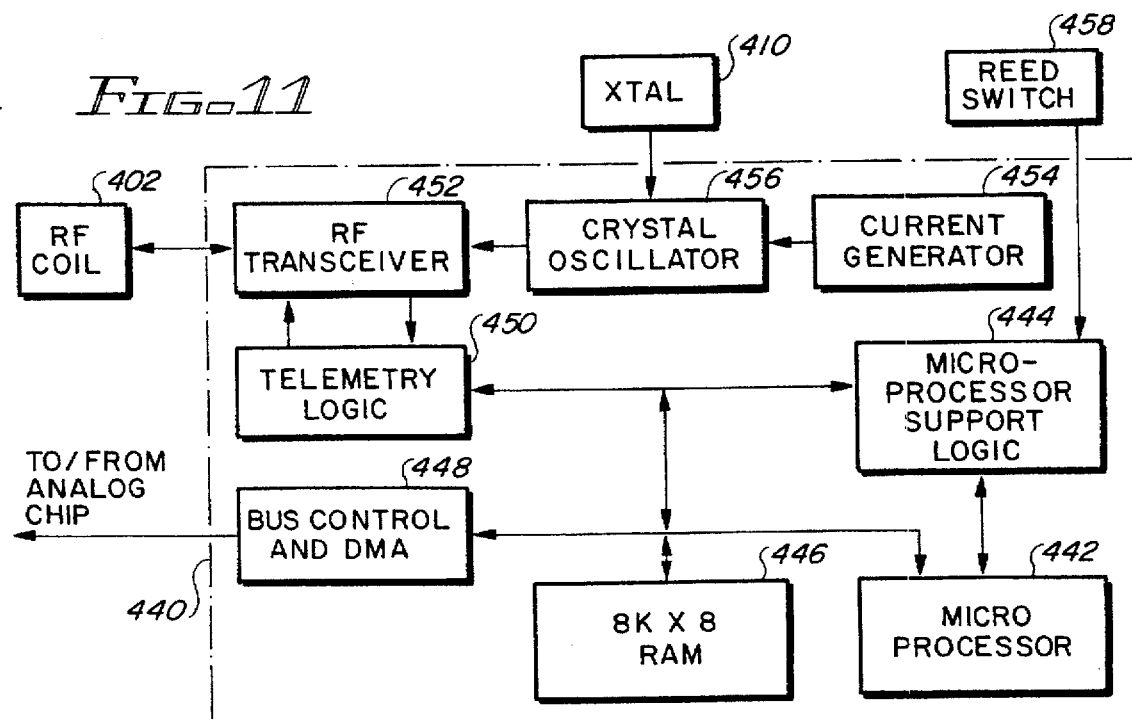
FIG. 11 is a block diagram of the digital chip portion of the pacemaker of FIG. 9, and illustrates the use of a microprocessor to control the operation of the pacemaker.

Turning next to FIG. 11, it is seen that the main control element of the pacemaker is a microprocessor 442, which microprocessor is included within the digital chip 440. The digital chip 440 contains all the necessary logic to interface the analog chip 420 with the internal microprocessor 442. The microprocessor 442 includes a basic CPU (central processing unit) and 8K of static RAM (random access memory). In addition, an 8K by 8K RAM 446 is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide DMA timing and control of data transfer with the analog chip 420, including timing and control of the analog-to-digital converter 432 (FIG. 10) and telemetry data. Telemetry channel logic 450 contains clock logic, IEGM and marker logic, telemetry command protocol logic, telemetry interrupt logic, error checking logic and CPU reset logic. An RF transceiver 452, coupled to the RF coil 402, transmits and receives telemetry data from the external programmer 48 through the telemetry head 49 (see FIG. 9). A crystal oscillator circuit 456, in conjunction with the crystal 410 (external to the digital chip 440) provides the crystal time base of the pacemaker system. A current generator 454 provides the bias currents for the digital chip. A reed switch circuit 458 detects the presence of a magnetic field, which magnetic field is present whenever the telemetry head 49 is in place on the patient's skin above the location where the pacemaker is implanted.

The pacemaker circuitry described in connection with FIGS. 9–11 above provides the basic functions of the pacemaker described in connection with FIG. 1, plus other pacing/sensing functions as are known in the art. For purposes of the present invention, the pacemaker circuitry of FIGS. 9–11 sets the basic timing of the pacing interval, including setting an AV interval and a VA interval. The circuitry also provides for sensing or detecting natural ventricular events (R-waves) and/or natural atrial events (P-waves), and for measuring the time interval between a sensed or paced atrial event and a natural ventricular event (R-wave). Such AR/PR time interval, as indicated previously, comprises the natural conduction time of the patient's heart. Once the natural conduction time has been determined, then the invention sets the AV (or PV) interval of the pacemaker to a value that is equal to the natural conduction time plus or minus a prescribed amount $\Delta 1$. In this way, then, the pacemaker's AV (or PV) interval automatically tracks the natural conduction time of the patient. Having altered the AV (or PV) interval by an amount $\Delta 1$, the pacemaker may also (in some modes) alter the VA interval by an amount $\Delta 2$ in the opposite direction, so that the sum of the altered AV and VA intervals remains unchanged.

By way of example, assume that the overall pacing interval, or A-to-A interval, which is equal to the AV interval plus the VA interval, is set to equal 1000 msec. Assume further that the AV interval is initially programmed or set to 150 msec and the VA interval is thus initially set to 850 msec. Still further, assume that the AR interval (the natural conduction time) is measured to be 100 msec, and that the amount $\Delta 1$ (the amount by which the AV interval is to differ from the AR interval) is set to be 10 msec. For standard pacing (where a V-pulse is generated only if an R-wave does not occur before the timing out of the AV interval), the AV interval is thus set to: AV=AR+$\Delta 1$=110 msec. In accordance with the present invention, when the AV interval is set to a value equal to the AR interval plus an amount $\Delta 1$, the VA interval is automatically decreased by an appropriate amount $\Delta 2$ so that the sum of the AV and VA intervals still equals the desired A-to-A interval (1000 msec in this example). Mathematically, this relationship is expressed as:

$$T_{A-A}=(AR+\Delta 1)+(VA-\Delta 2)=AV+VA_A$$

where $T_{A-A}$ is the period of the desired pacing rate, or the A-to-A interval, AR is the measured natural conduction time, $\Delta 1$ is the amount by which the AV interval is to differ from the AR interval, AV is the set value of the AV interval (=AR+$\Delta 1$), VA is the programmed VA interval, and $VA_A$ is the adjusted value of the VA interval. For the example above, it is thus seen that if the AV interval is set to 110 msec, then the VA interval would be adjusted to 890 msec, and $\Delta 2$ would be equal to 40 msec (890−850=40). Similarly, if the AV interval is decreased by the amount $\Delta 1$, then the VA interval is increased by a computed or calculated amount $\Delta 2$ so that the sum of the modified AV and VA intervals still equals the desired A-to-A interval, or mathematically:

$$T_{A-A}=(AR-\Delta 1)+(VA+\Delta 2).$$

Thus, it is seen that the VA interval is automatically changed to compensate for variations that occur in the AV interval (as a result of variations in the AR interval) in order to keep the overall A-to-A interval unchanged.

Referring next to FIG. 2, a block diagram of an alternative embodiment of the control circuit or system 26 of the pacer 10 (FIG. 1) is illustrated. It is noted that in addition to the embodiment of the invention illustrated above in FIGS. 9–11, or below in FIG. 2, that still other embodiments of a control system 26 may be utilized. The embodiment described above in FIGS. 9–11 shows a control system and pacemaker configuration that is based on a microprocessor. Another representative microprocessor-based system is described, for example, in U.S. Pat. No. 4,940,052, entitled "Microprocessor Controlled Rate-Responsive Pacemaker Having Automatic Threshold Adjustment," incorporated herein by reference.

The control system shown in FIG. 2 is based on a state machine wherein a set of state registers 60 define the particular state of the pacer at any instant in time. As is known in the art, state machines may be realized using dedicated hardware logic circuits, or a suitable processor (programmed-controlled circuit) to simulate such dedicated hardware logic circuits. However implemented, the results are the same—the state of the pacer is defined at any instant of time by the pacemaker logic and sensed events which transpire or fail to transpire, such as the sensing of an R-wave, or the timing out of a timer. A complete description of FIG. 2, including basic state machine operation, may be found in the patent applications that have previously been incorporated herein by reference. The various circuits of the control system 26 of FIG. 2, or simulated equivalents thereof, may be conventional, or may be patterned after known circuits available in the art. Reference is made, for example, to U.S. Pat. No. 4,712,555 wherein a state-machine type of operation for a pacemaker is described; U.S. Pat. No. 4,788,980, wherein the various timing intervals used within the pacemaker and their inter-relationship are more thoroughly described; and U.S. Pat. No. 4,944,298 wherein an atrial-rate based programmable pacemaker is described, including a thorough description of the operation of the state logic used to control such a pacemaker. The '555, '980 and '298 patents are also incorporated herein by reference. It is noted that portions of one embodiment of the control system 26 that specifically relate to AV adjustment features of the present invention are further described below in conjunction with FIGS. 6 and 7.

The details of the control system 26, whether based on a microprocessor, state machine, or other type of control devices, or simulated control devices, are not critical to an understanding or implementation of the present invention, and hence are not presented herein. Such details may be found in the referenced applications and patents, if desired. All that is important for purposes of the present invention is that the control system of the pacemaker be capable, in conjunction with other pacemaker circuitry, of measuring the natural conduction time of the patient, or the AR interval. Such measurement can be made in conventional manner, and may involve an averaging of the AR interval over several cardiac cycles, e.g., for at least y cardiac cycles, or other computation or estimation of the AR interval as is known in the art. Once the AR interval has been measured, or otherwise determined, the pacemaker then sets its AV (or PV) interval to a value that is a prescribed amount less than or greater than the determined AR interval.

Figure 12:
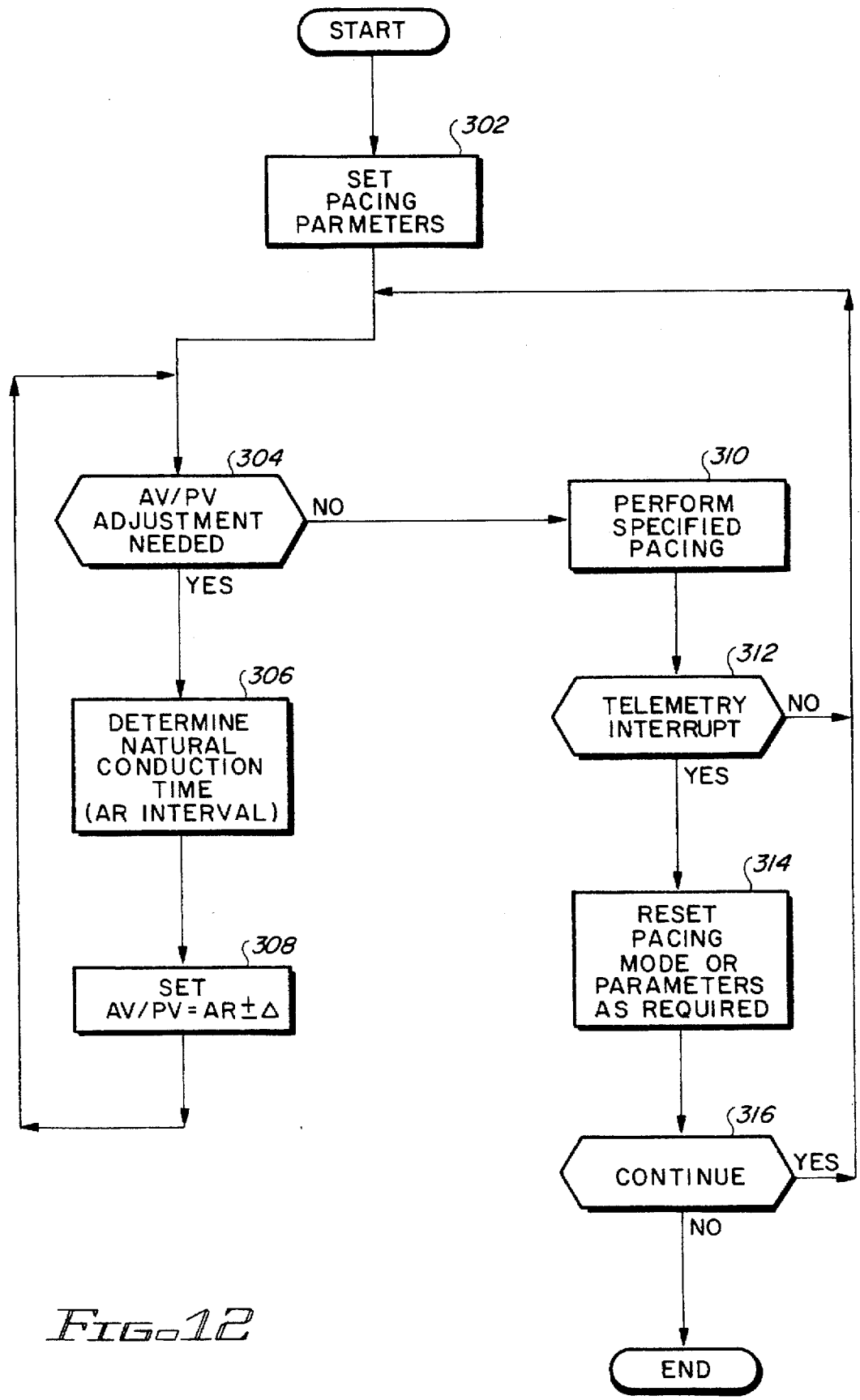
FIG. 12 is a flowchart illustrating the basic method carried out by a pacemaker of FIG. 9 in order to implement the present invention.

The above-described process—of determining the natural conduction time (AR interval), and setting the AV (or PV) interval to be a prescribed amount less than or greater than such AR interval—is illustrated further in the high level flow diagram of FIG. 12. In FIG. 12, and the other flow diagrams or flowcharts used herein, each main step of the process or sequence is shown as a "block" or "box", with each block having a reference numeral assigned thereto to aid in the explanation thereof. Such flowchart is particularly helpful when the invention is implemented using a microprocessor, or equivalent processing device, that follows a stored program, with the flowchart representing the stored program that is used by such processor.

As seen in FIG. 12, once the process has been started, an initial step involves setting the pacemaker parameters (block 302). Such parameters include, but are not limited to, the value Δ that is used to define the AV (or PV) interval once the natural conduction time, or AR interval, has been measured. Other pacing parameters include how often the AR interval should be determined, either as a function of elapsed time, or elapsed cardiac cycles. For example, a common parameter for this purpose would be to specify a variable x which represents the number of cardiac cycles that are to elapse between determinations of the AR interval. If AR pacing commonly occurs, i.e., if the ventricle of the heart is normally able to contract naturally, thereby eliminating the need for generating a V-pulse, the AR interval may simply be measured each time that an R-wave occurs. If ventricular pacing is more common, i.e., if a V-pulse is generated most cardiac cycles, then periodically, e.g., every x cardiac cycles, generation of the V-pulse in its normal time sequence may have to be inhibited to allow an AR measurement to be made. Other pacing parameters are as conventionally used, e.g., pacing mode, base pacing rate, stimulation energy, sensitivity, etc., in any pacing application.

Once the pacing parameters have been set, a determination is made as to whether it is time to update the setting of the AV (or PV) interval. Typically, as indicated above, the natural conduction time, or AR interval, may simply be measured each time that an R-wave occurs. If no R-waves occur for a prescribed number x of cardiac cycles, then the natural conduction time (AR interval) is determined (block 306). Once determined, the AV (or PV) interval is updated to be equal to the AR interval ±Δ (block 308).

If it is not time to update the AV (or PV) interval (NO branch of block 304), then the specified pacing modality is carried out in conventional manner (block 310) until such time as a determination is made that the AV (or PV) interval should be adjusted (blocks 310, 312, 304).

At any time during the specified pacing, a telemetry interrupt signal may be received (block 312), or equivalent, indicating that the physician, or other medical personnel, have coupled an external programmer 48 (FIGS. 1 or 9) to the pacemaker, and desire to monitor the operation of the pacemaker or alter the programming of the pacemaker. (Such interrupt signal, in some instances, may be effected by simply the closure of a magnetic reed switch within the pacemaker as a result of placing a magnet, associated with the external programmer, near the pacemaker.) If such an interrupt signal, or equivalent, is received, then appropriate action is taken, e.g., the pacing mode is reset, or the pacing parameters are altered, etc. (block 314), in conventional manner. After the specified telemetry action is completed, and if (as a result of the telemetry action or reprogramming) the pacemaker is to continue (block 316) with the adjustment of the AV (or PV) interval as a function of the measured AR interval, then the process repeats.

Figure 13:
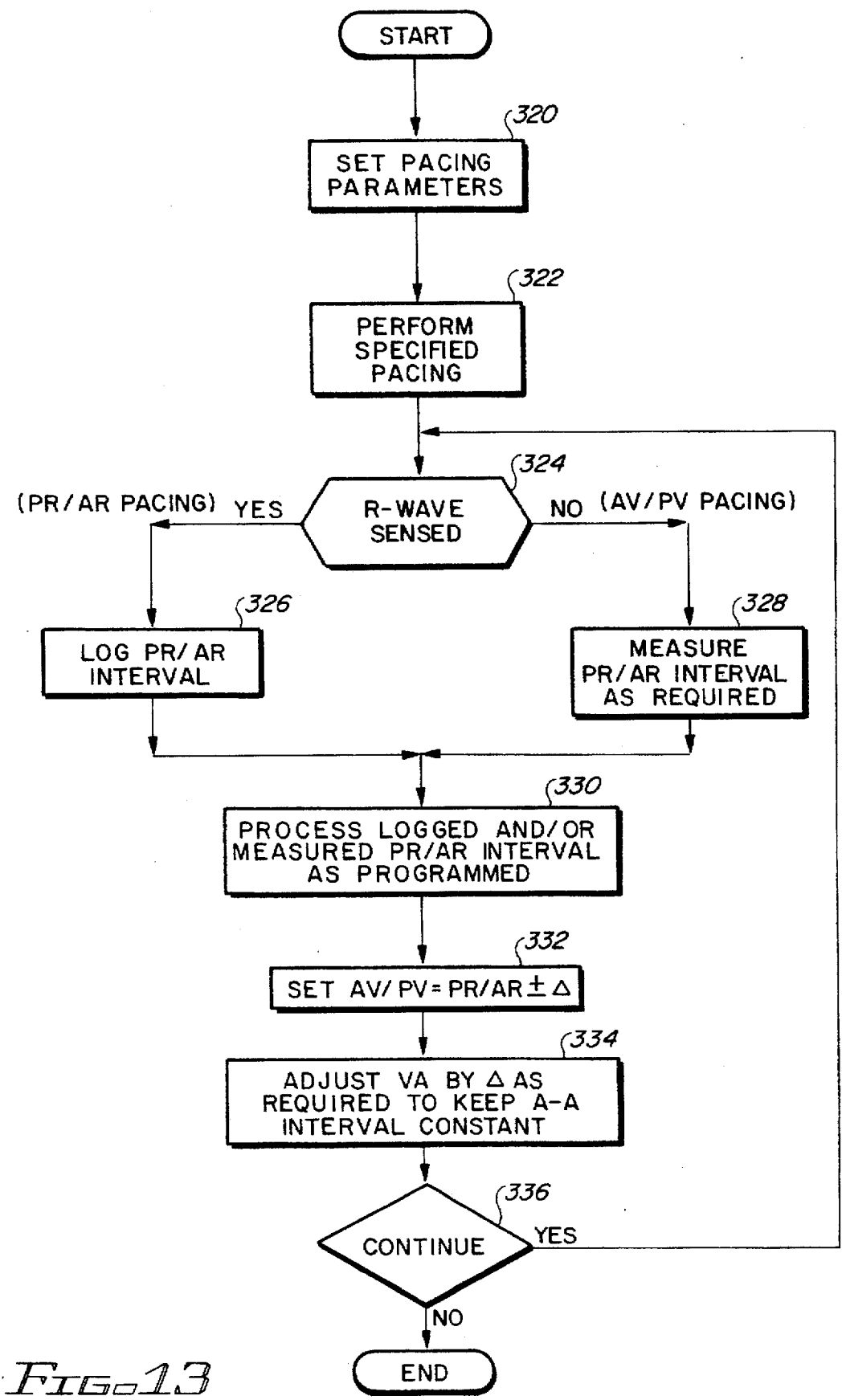
FIG. 13 is a flowchart that illustrates one technique used by the pacemaker of FIG. 9 to determine the natural conduction time, and to use such determination to set the AV (and PV) intervals of the pacemaker, as well as to make adjustments, when needed, to the VA interval of the pacemaker.

A preferred technique for measuring the natural conduction time, and using it to update the AV (or PV) interval is as illustrated in the flow diagram of FIG. 13. As seen in FIG. 13, once the pacing parameters have been set (block 320), the appropriate programmed pacing is carried out (block 322). Such pacing is typically atrial-based or ventricular-based. In atrial-based pacing, the occurrence of an atrial event starts the appropriate timers that define the duration of the basic cardiac cycle, or A-A interval. The A-A interval includes the AV interval and an atrial escape interval, AEI, both of which are keyed off of, or start, upon the occurrence of an atrial event, i.e., either the sensing of a P-wave or the generation of an A-pulse. In ventricular-based pacing, in contrast, the basic pacing cycle, or A-A interval, includes the AV interval followed by a VA interval. The AV interval begins upon the occurrence of an atrial event, either a P-wave or an A-pulse. The VA interval begins upon the occurrence of a ventricular event, either an R-wave before the timing out of the AV interval, or the generation of a V-pulse upon the timing out of the AV interval. Thus, when an R-wave occurs, the VA interval begins sooner in the cardiac cycle than it would have had the R-wave not occurred, and the basic A-A interval that defines the basic cardiac cycle is made shorter.

Still referring to FIG. 13, if an R-wave is sensed (block 324) while the pacer is carrying out its programmed pacing mode (block 322), then the AR (or PR) interval (the conclusion of which is marked by the R-wave) is simply logged or otherwise recorded (block 326). Such AR interval represents the natural conduction time. If an R-wave is not sensed (block 324) while the pacer is carrying out its programmed pacing mode (block 322), then the natural conduction time, or AR interval, is measured (block 328), as required, using the pacing parameters that were initially set (block 320). For example, if x cardiac cycles have gone by, where x is an integer, e.g., between 4 and 512, without an R-wave having been sensed, then a forced measurement of the AR interval is made by extending the AV interval sufficiently long in the next cardiac cycle to assure that an R-wave will most likely occur, which R-wave will then provide a basis for measuring the natural conduction time.

Once the natural conduction time has been determined, whether logged as a result of the natural occurrence of an R-wave (block 326) or measured as a result of a forced extension of the AV interval (block 328), then the logged or measured natural conduction time is processed as programmed (block 330). Such processing may be as simple as using the last AR interval that was determined, whether logged (block 326) or measured (block 328). Other processing schemes may include maintaining a simple running average of the last k AR intervals that have been logged or measured, where k is an integer of between, e.g., 2 and 20; or of computing a statistical mean of the AR interval over the last k AR interval determinations. Yet other processing schemes, aimed at providing a true measure of the AR interval over a prescribed period of time may also be used.

Once the AR interval has been determined (blocks 326, 328), and has been appropriately processed (block 330), then the AV (or PV) interval is simply set to a value that is equal to the determined AR interval, plus or minus a prescribed amount, Δ (block 332). The parameter Δ (also referred to herein as Δ1) is a programmable number that is typically between 1 and 100 msec. Whether the amount Δ is added to the AR interval, or subtracted from the AR interval, in order to set the AV/PV interval, is controlled by the pacing parameters that are initially loaded into the pacemaker (block 320). Further, if desired, two values of Δ may be used, a first ΔS that is subtracted from the AR interval, and a second ΔA that is added to the AR interval. Thus, by careful selection of such pacing parameters, the patient's physician or cardiologist is able to control the manner in which the AV/PV interval tracks the AR interval that is uniquely suited to the needs of a particular patient.

Once the AV/PV interval has been set (block 332), then the VA interval may be adjusted by an appropriate amount Δ2, as required, in order to keep the overall A-A interval constant. Typically, such adjustment (block 334) is only needed when in a ventricular-based pacing mode. Thus, for example, if operating in a ventricular-based pacing mode, and if the AV/PV interval is shortened by an amount Δ1 (block 332), then the VA interval is lengthened by an appropriate amount Δ2 (block 334) so as to maintain the same basic time for the A-A interval. Similarly, if operating in a ventricular-based pacing mode, and if the AV/PV interval is lengthened by an amount Δ1 (block 332), then the VA interval is shortened by an appropriate amount Δ2 (block 334) so as to maintain the same basic time for the A-A interval. When operating in an atrial-based pacing mode, there is no need to adjust any timing intervals because both the AV interval and AEI are keyed off of an atrial timer.

Once the AV/PV interval has been set (block 332), and the VA interval has been adjusted, if required (block 334), and assuming the specified pacing is to continue (block 336), the process repeats (blocks 322–334) so that the AV/PV interval is set to value that tracks the natural conduction time of the patient.

As mentioned above, the present invention contemplates two modes of AV (or PV) adjustment. In a first mode, the AV interval is always set to be just a little bit longer than the natural conduction time of the patient's heart, i.e., just a little bit longer than the AR interval, so that the patient's heart is afforded as much opportunity as possible to beat on its own without applying a ventricular stimulus (V-pulse). In the first mode, the AV interval is thus set to be equal to the AR interval plus a prescribed amount Δ1. In a second mode, the AV interval is always set to be just a little bit shorter than the natural conduction time of the patient's heart, i.e., just a little bit shorter than the AR interval, thereby assuring that a V-pulse is most always provided. In the second mode, the AV interval is thus set to be equal to the AR interval minus an prescribed amount ΔS. Such second mode is particularly well suited for patient's suffering from certain cardiac disorders, such as cardiomyopathy, because the applied V-pulse significantly improves the patient's cardiac output. The prescribed amounts Δ1 and ΔS may be equal to each other, or they may be different, depending upon the particular patient and type of pacing therapy that is being applied. In either mode, it is desirable that the AV interval be set to a value that is different than the AR interval value so as to avoid fusion. Thus, depending upon the selected mode, the AV adjustment operation of the present invention uses the most recently determined AR interval value to guide the selection of the next AV (or PV) interval value during the next (or a subsequent) cardiac cycle.

As also indicated above, the determination of the AR interval, or natural conduction time, may be made by simply monitoring the time interval between an atrial event, whether a P-wave or an A-pulse, and the occurrence of an R-wave. While such AR interval measurement is being performed, the AV (or PV) interval of the pacemaker may be temporarily set (e.g., for one cardiac cycle) to a value that is sufficiently long in most instances to assure the occurrence of an R-wave within the cardiac cycle. Further, in order to avoid reliance on a single AR interval measurement, which single AR interval measurement may not represent a true measure of the natural conduction time due to a premature ventricular contraction, or due to an erratic heartbeat, of for other reasons, the determination of the AR interval preferably involves taking an average, or other estimation, of the AR interval based on measuring the AR interval more than once, i.e., over more than one cardiac cycle.

Other techniques, of course, may also be used to determine the natural conduction time of the patient, including determining a mean of the AR interval, or performing other processing of a family of prior AR interval measurements. Alternatively, the AR interval may be determined as the "cross-over" point that occurs when the AV interval is incrementally increased or decreased in known step sizes until a point is reached at which the AV interval crosses over from being less than the natural conduction time, or more than the natural conduction time. The goal of such processing or measurements, whatever they may be, is that the AR interval determination, from which the AV (or PV) intervals are set, represents an accurate determination of the patient's natural conduction time.

Turning next to FIG. 3, one manner in which the AV interval is adjusted by the present invention is illustrated. Shown in FIG. 3 is an "event line" 90 that depicts the cardiac events that may occur during a cardiac cycle. Such events are depicted by way of pulses, e.g., A-pulses 92, 93, or depolarization signals, e.g., an R-wave 94, or repolarization signals, e.g., a T-wave 96 (representing the repolarization of the ventricles), and thus are shown in a manner similar to how such events might appear in an intracardiac electrogram (EGM) signal, or a skin electrocardiographic (ECG) signal. However, for purposes of the present invention, it should be noted that the event line 90 is not intended to be an accurate representation of either an EGM or an ECG signal; rather, it is intended simply to diagrammatically depict the events that occur in a given cardiac cycle.

From FIG. 3, it is seen that the "cardiac cycle" comprises the time interval from atrial activity to the next atrial activity, e.g., from A-pulse 92 to the next A-pulse 93. The cardiac cycle may just as easily comprise, or be measured as, the time interval between ventricular activity and the next ventricular activity, e.g., from R-wave 94 to the next R-wave (or V-pulse) that occurs in the event line 90. However, such next R-wave (or V-pulse) is not shown in the event line 90 of FIG. 3, so the cardiac cycle is shown as the time between the A-pulses 92 and 93.

As seen in FIG. 3, the AR interval is shown as the time interval in the cardiac cycle following atrial activity (the A-pulse 92 for the condition shown in FIG. 3) to the occurrence of natural ventricular depolarization (the R-wave 94). Such AR interval thus represents the natural conduction time of the heart, i.e., the time it takes an atrial stimulus to travel to the ventricles through the atrioventricular (AV) node and the atrioventricular (AV) bundle. In order to avoid fusion, it is desirable that the AV interval of the pacemaker be set to a value different than the natural conduction time, or AR interval. The present invention accomplishes this by either setting the AV interval to a value that is shorter than the AR interval by an amount Δ1, or setting the AV interval to a value that is longer than the AR interval by an amount Δ2.

Further, for some applications of the invention, it is desirable to find a cross-over point, i.e., the point where the AV interval crosses over from being just less than the AR interval to being more than the AR interval; or the point where the AV interval crosses over from being just more than the AR interval to being just less than the AR interval. Such cross-over point will typically represent an accurate determination of the natural conduction time, and therefore a reliable basis from which the AV (or PV) interval may be set to be more than, or less than, such natural conduction time.

In a first adjustment mode contemplated by the present invention, the end goal is to have the AV interval longer than the AR interval, but not too much longer, so that the heart is afforded every opportunity to depolarize on its own without the necessity of a V-pulse. The reason that the AV interval should not be too much longer than the AR interval is because the natural conduction time (AR interval) will change somewhat to meet the physiological needs of the patient, and it is desirable to provide the V-pulse at a time in the cardiac cycle that tracks such needs. A simple way to achieve this goal, as indicated above, is to measure the AR interval and set the AV interval to a value equal to the AR interval plus an amount $\Delta$. Another way to achieve his goal is to initially set the AV interval to a very short value, and incrementally increase it, at prescribed intervals, e.g., every cardiac cycle, until it crosses over the AR interval. The cross-over point is detected by monitoring the ventricular channel for the occurrence of an R-wave during each prescribed interval. That is, during the AV interval adjustment sequence, the AV interval is first set to a value much shorter than the AR interval, thereby assuring the generation of a V-pulse as the ventricular activity in the cardiac cycle. As the AV interval is increased, the V-pulse will continue to be generated for so long as the AV interval remains less than the AR interval. As soon as the AV interval becomes longer than the AR interval, an R-wave occurs, and the generation of the V-pulse is inhibited. Thus, for an AV interval that starts at a short value and is gradually increasing, the cross-over point is detected when an R-wave first occurs.

In a second adjustment mode contemplated by the present invention, the end goal is to have the AV interval shorter than the AR interval, but not too much shorter, so that a V-pulse is always provided during the cardiac cycle. Such mode may be used, for example, for patients suffering from a cardiomyopathy, as described in Applicant's copending patent application, previously referenced. A simple way to achieve this end goal, as indicated above, is to measure the AR interval and set the AV interval to a value that is a prescribed amount $\Delta$ less than the measured AR interval. Another way to achieve this goal is to initially set the AV interval to a very long value, forcing R-waves to occur, and then incrementally decreasing it, at prescribed intervals, e.g., every cardiac cycle, until it crosses over the AR interval. The cross-over point is detected when R-waves first cease to occur.

The AV interval will be approximately the same as the AR interval at the cross-over point, although there will normally be some difference between the two values as a function of how much the AV interval changes during each step of an adjustment cycle. Thus fusion will normally be avoided by simply using the AV interval value at the cross-over point. To further assure that fusion is avoided, however, the present invention typically adds on appropriate AV margin, e.g., an amount $\delta$, to the AV interval determined at the cross-over point.

The incremental process of adjusting the AV interval in accordance with the first AV interval adjustment mode mentioned above (i.e., making it short and incrementally increasing it until the cross-over point is reached) is further illustrated in FIG. 4. Similarly, incremental process of adjusting the AV interval in accordance with the second AV interval adjustment mode mentioned above (i.e., making it long and incrementally decreasing it until the cross-over point is reached) is further illustrated in FIG. 5. A detailed explanation of the processes shown in FIGS. 4 and 5 may be found in applicant's copending parent patent application, Ser. No. 07/976,153, filed Nov. 13, 1992, now U.S. Pat. No. 5,344,220, previously incorporated herein by reference.

Turning next to FIG. 6, a functional block diagram is illustrated of the pacemaker components that may be used to carry out the adjustment of the AV interval in accordance with the present invention, and particularly when the AV interval is incrementally adjusted as shown in FIGS. 4 and 5. It is noted that most of the components shown in FIG. 6 are included in the control system 26 or memory 40 (FIG. 1). Such components may be considered part of the state logic 62, programmable timer 76, and/or T.O. Decode Logic 78 (FIG. 2); or as part of the microprocessor 442 and microprocessor support logic 444 (FIG. 11). It is noted that the function performed by the components shown in FIG. 6 can be achieved using numerous hardware and/or microprocessor-based configurations. That which is shown in FIG. 6 is merely exemplary of one such configuration.

As seen in FIG. 6, the memory 40 includes addressable locations therein that contain various data and parameters used during operation of the pacemaker. One set of such parameters may be the various AV interval incremental values, $AV_{MIN}$, AV1, AV2, ... AVn, $AV_{MAX}$, or the $\Delta A$, $\Delta S$ values, that may be used when adjusting the AV interval. Such set of values are then retrieved, as required when an AV adjustment is needed, and loaded into an AV register 160 and an AV timer 162. The AV timer 162 is used to define the AV interval by loading the desired AV interval value therein and counting down to zero, issuing an appropriate time-out (T.O.) signal when the countdown has been completed. Alternatively, in the event an R-wave occurs before the AV interval has timed-out, the count remaining in the AV timer 162 provides a measure of the AR interval, or conduction time. Such AR interval, as mentioned previously, comprises the natural conduction time of the patient. If an incremental adjustment scheme is used, as shown in FIGS. 4 or 5, then the initial value of the AV interval, loaded in the register 160, is compared to the AR interval in order to ascertain the difference between the two values. Such difference may be used to steer the selection of the next AV value, thereby providing a truly adaptive adjustment of the AV interval. If a simple adjustment scheme is used, as described in conjunction with FIG. 13, then the AR interval held in the timer 162 is processed, as required, to average it, etc., so that it represents an accurate measure of the natural conduction time, and then the value of $\Delta A$ or $\Delta S$ is retrieved from memory, added to or subtracted from the processed value of the AR interval, with the value thus obtained being loaded into the register 160. In this way, the AV interval is simply set to the value of the AR interval $\pm \Delta$.

Operation of the AV register 160 and the AV timer 162 is controlled by the AV adjustment logic 164. Basically, included in such logic is a means for detecting the occurrence of atrial activity. Such means are functionally represented in FIG. 6 by the OR gate and the A-V latch 168. The occurrence of either a P-wave, represented by the signal "IPW", or the occurrence of an "A-Trig" signal (used to trigger the APG 18 in FIG. 1 to generate an A-pulse) are sensed by the OR gate 166, with either event causing the A-V latch to be set. Similarly, the occurrence of either an R-wave, represented by the signal "IRW", or the occurrence of a "V-Trig" signal (used to trigger the VPG 20 in FIG. 1 to generate a V-pulse) are sensed by OR gate 170 to reset the A-V latch 168. Thus, during the AV interval portion of a cardiac cycle, the A-V latch 168 is set, and during the V-A interval portion of a cardiac cycle, the A-V latch 168 is reset.

In carrying out the stair-step adjustment sequences shown in FIGS. 4 and 5, it is noted that the output of the OR gate 170 also serves as a cardiac cycle clock signal, which cycle clock signal is counted in a cycle counter 172. Such cycle counter 172 is used to define the search time $T_S$, as well as to check the time that elapses between AV adjustment sequences, $t_A$. The cycle clock signal is further used to clock a two-bit register 174 that monitors the type of ventricular activity (V-pulse or R-wave) that occurred during the last two cardiac cycles. If the current cardiac cycle contains an R-wave, as indicated by the IPW signal, then such signal sets the first bit to a "1". If the current cardiac cycle contains a V-pulse, as indicated by the V-Trig signal, then such signal sets the first bit to a "0". At the occurrence of the next cardiac cycle, this bit is shifted to the second bit of the register, and the first bit is set appropriately to indicate the type of ventricular activity in the new current cardiac cycle. Thus, in this manner, the register 174 always contains an indication of the type of ventricular activity that occurred during the two most recent cardiac cycles.

An Exclusive OR gate 176 checks the contents of the register 174 to detect if a change has occurred. If the present cardiac cycle includes an R-wave, whereas the cardiac cycle immediately preceding the present cardiac cycle contained a V-pulse, then the output of the Exclusive OR gate 176 will be a "1", indicating that a change occurred in the type of ventricular activity. Similarly, if the present cardiac cycle includes a V-pulse, whereas the cardiac cycle immediately preceding the present cardiac cycle contained an R-wave, then the output of the Exclusive OR gate 176 will also be a "1", indicating that a change occurred in the type of ventricular activity. However, if the two most recent cardiac cycles both contained a V-pulse, or both contained an R-wave, then the output of the Exclusive OR gate 176 will be a "0", indicating that no change occurred in the type of ventricular activity over the last two cardiac cycles.

Logic circuitry 178 within the AV adjustment logic 164 monitors the A-V Latch 168 (represented by an Activity signal), the cycle counter 172, and the Exclusive OR gate 176 (represented by a V-Channel change signal), in conjunction with the contents of the AV timer 162 and the AV register 160, in order to carry out the AV adjustment sequences described above.

Figure 7:
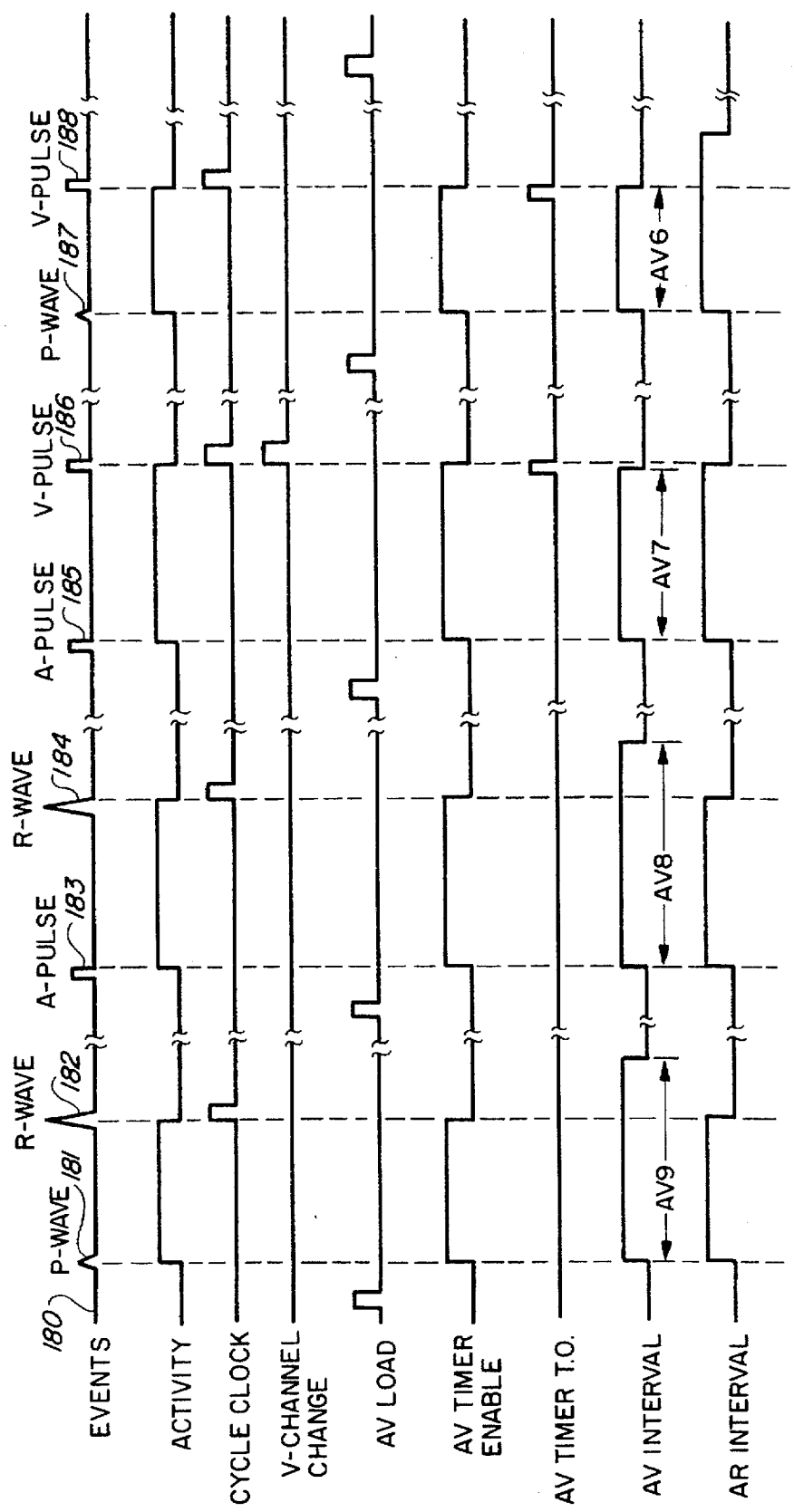
FIG. 7 is a timing diagram that illustrates some of the signals associated with the operation of the circuitry of FIG. 6.
Figure 8A:
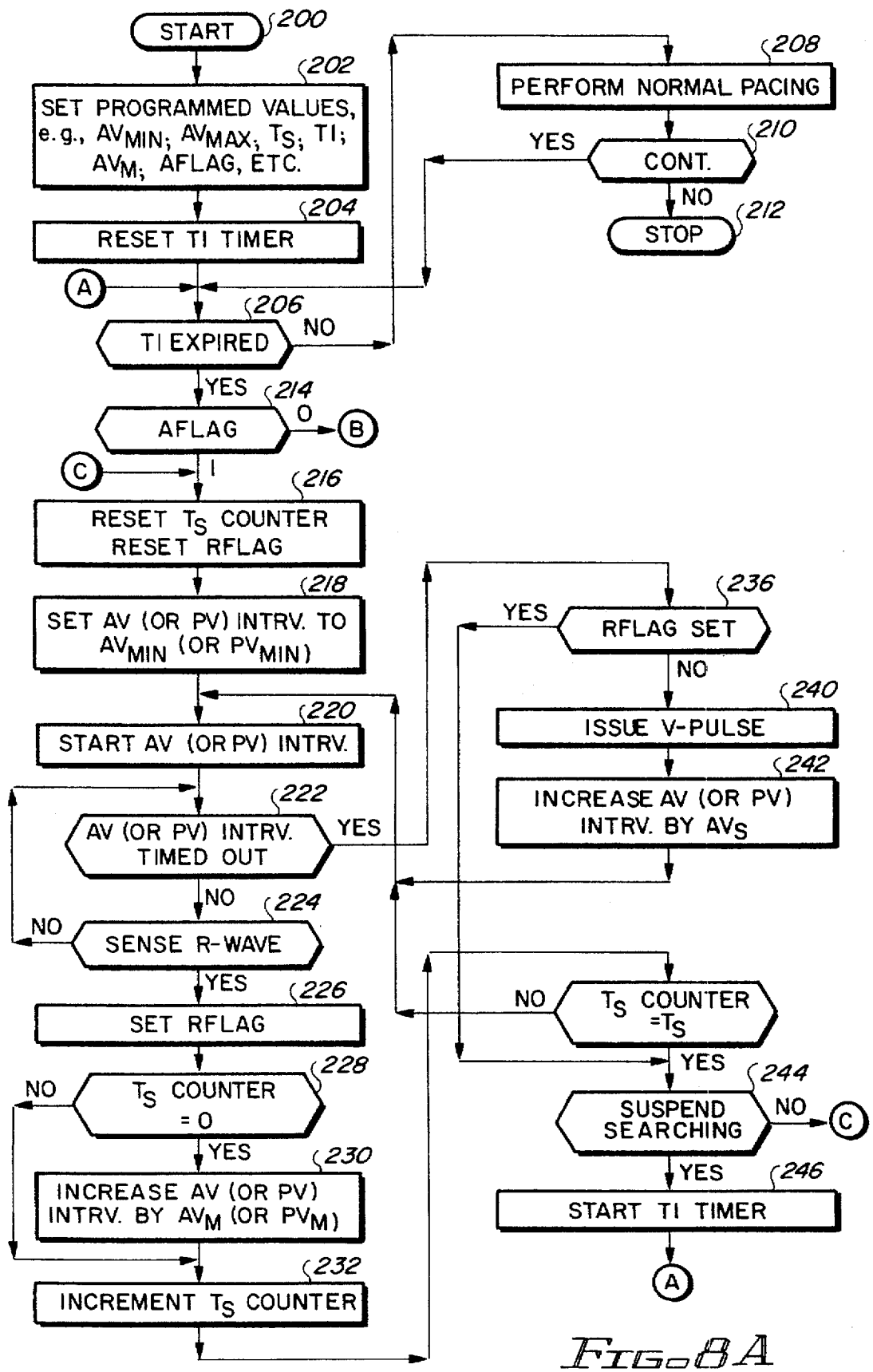
FIGS. 8A and 8B show a flowchart that illustrates one method that may be used to carry out the adjustment methods illustrated in FIGS. 4 and 5.
Figure 8B:
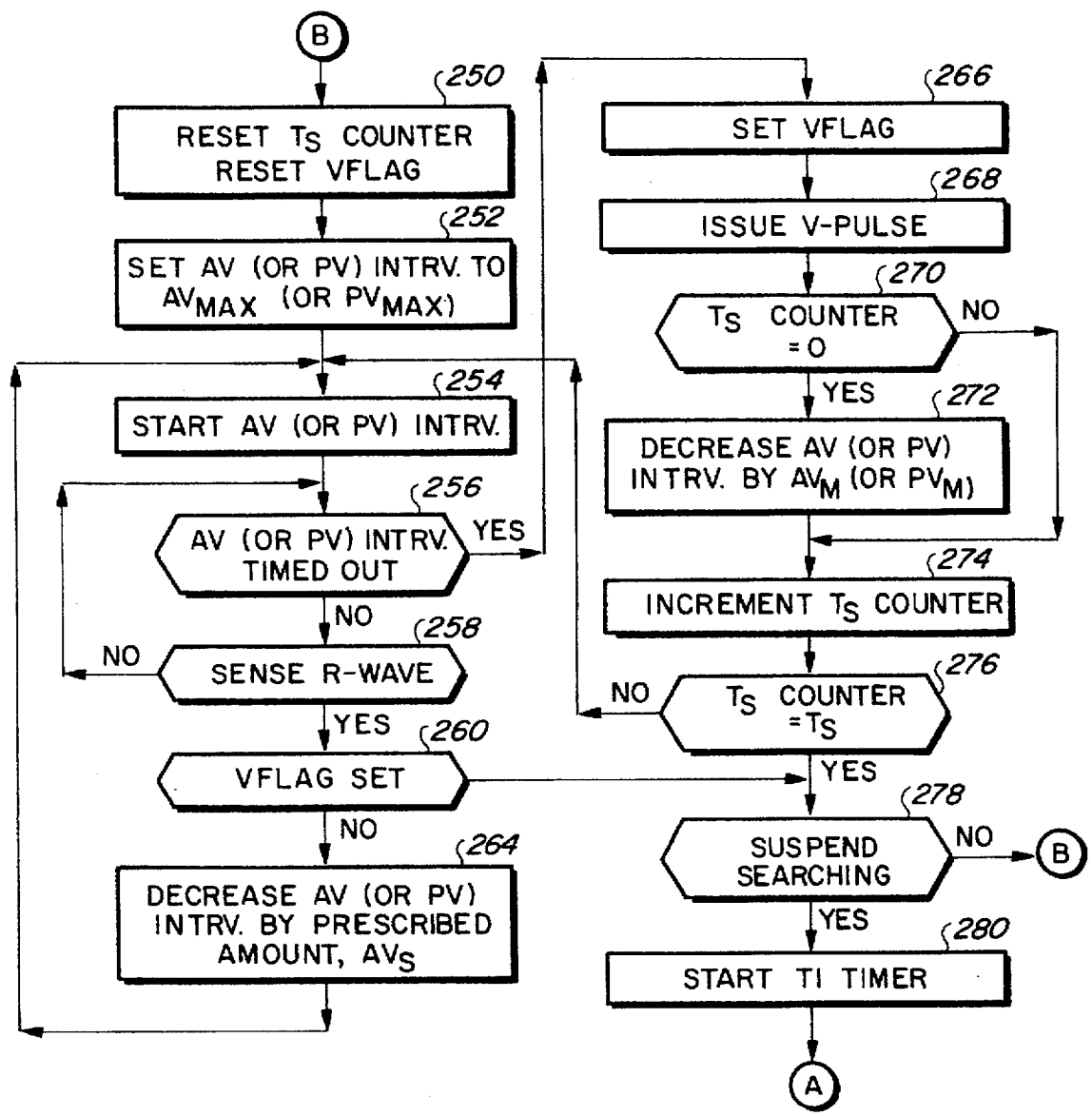

The above process, when used to incrementally adjust the AV interval as shown in FIGS. 3, 4 or 5, is further illustrated with reference to the timing waveform diagram of FIG. 7, and the flowcharts or flow diagrams of FIGS. 8A and 8B. The timing waveform diagram of FIG. 7 is associated with the operation of the circuitry of FIG. 6. The flowcharts of FIGS. 8A and 8B show further details concerning the incremental AV adjustment illustrated in FIGS. 4 and 5. As the present invention is directed primarily to the simplified AV adjustment approach of measuring the AR interval, and setting the AV/PV interval to a value equal to the AR interval ±Δ, as described above in connection with the description of FIGS. 1 and 9–13, a detailed description of FIGS. 7, 8A and 8B will not be presented herein. Such detailed explanation may be obtained in the parent patent application, Ser. No. 07/976,153, now U.S. Pat. No. 5,334,220, previously incorporated herein by reference.

As described above, it is thus seen that the present invention provides an implantable pacemaker that automatically adjusts its AV (or PV) interval to a value that is a prescribed amount less than, or a prescribed amount greater than, the natural conduction time of a patient's heart. Hence, while the AV (or PV) interval tracks changes in the natural conduction time, it is always set to a value that is different than the natural conduction time by a small amount.

As further described above, it is seen that the invention provides such adjustment of the AV interval while avoiding fusion, i.e., the issuing of a V-pulse on top of an R-wave.

While the invention herein disclosed has been described by means of specific embodiments and applications thereof, numerous modifications and variations could be made thereto by those skilled in the art without departing from the scope of the invention set forth in the claims.

What is claimed is:

1. A method of operating a dual-chamber implantable pacemaker, the pacemaker having sensing means for sensing atrial and ventricular activity, generating means for generating atrial and ventricular stimulation pulses, and timing means for setting an AV interval that defines the maximum time permitted by the pacemaker after atrial activity before a ventricular stimulation pulse (V-pulse) is generated, and wherein sensed atrial activity comprises a natural atrial depolarization (P-wave) and sensed ventricular activity comprises a natural ventricular depolarization (R-wave), the method comprising:

(a) sensing P-waves and R-waves with the sensing means;

(b) generating atrial and ventricular stimulation pulses with the generating means for maintaining a specified cardiac rhythm;

(c) determining an AR interval as the time interval between atrial activity and a sensed R-wave, where atrial activity comprises either a sensed P-wave or the generation of an atrial stimulation pulse (A-pulse) by the generating means, whichever occurs first in a given cardiac cycle; and (d) setting the AV interval of the pacemaker to be equal to the determined AR interval ± þ, where þ is a time increment ranging from 1 to 100 msec.

2. The method of claim 1 wherein step (a) comprises determining an average AR interval over k cardiac cycles, where k is an integer between 2 and 1024, and wherein step (b) comprises setting the AV interval to be equal to the average AR interval ±Δ.

3. The method of claim 1 wherein step (c) comprises (1) defining a cardiac cycle; (2) sensing whether an R-wave occurs in the defined cardiac cycle; (3) using as the determined AR interval the AR interval of the defined cardiac cycle when an R-wave occurs therein, (4) in the event an R-wave does not occur in the defined cardiac cycle, defining a subsequent cardiac cycle as one wherein an R-wave does occur, and (5) measuring an AR interval of the subsequent cardiac cycle as the determined AR interval.

4. The method of claim 3 wherein the step of defining the subsequent cardiac cycle comprises sensing whether an R-wave occurs during each defined cardiac cycle, waiting for at least x consecutive cardiac cycles without an R-wave having been sensed, and then monitoring each cardiac cycle thereafter until an R-wave is sensed, where x is an integer from 4 to 512, the first cardiac cycle during which an R-wave is sensed after waiting at least x cardiac cycles comprising the subsequent cardiac cycle.

5. The method of claim 1 wherein the pacemaker further has a VA interval that, in sequential combination with the AV interval, defines the duration of an A-to-A interval, or pacing cycle, and wherein variations in the determined AR interval cause corresponding variations in the AV interval, and wherein the method further comprises:

(e) setting a VA interval of the pacemaker to a value that compensates for the variations in the AV interval in order to assure that the A-to-A interval does not change.

6. A method of stimulating cardiac tissue using an implanted dual-chamber pacemaker, the pacemaker having means for sensing atrial and ventricular events, and means for generating a ventricular stimulation pulse (V-pulse) and delivering the V-pulse to a prescribed ventricular location, said method comprising:

(a) sensing atrial and ventricular events in each cardiac cycle;

(b) determining a natural conduction time of the cardiac tissue by sensing both an atrial event and a natural ventricular event (R-wave) within the same cardiac cycle, and defining the natural conduction time as the time interval between the sensed atrial event and the sensed R-wave; and (c) generating and delivering the V-pulse to the prescribed ventricular location at a time following a sensed atrial event in each cardiac cycle in which an R-wave is not sensed that is a prescribed amount þ different from the natural conduction time last determined in step (b), whereby the natural conduction time determines when the V-pulse is generated in each cardiac cycle not having a sensed R-wave.

7. The method of claim 6 further including determining the natural conduction time as set forth in step (b) pursuant to a prescribed schedule that comprises determining the natural conduction time after x cardiac cycles have elapsed, wherein x is an integer of from 4 to 512.

8. The method of claim 7 wherein step (b) comprises determining whether an R-wave is sensed or not; and, if an R-wave is sensed, measuring the duration of an AR interval that begins with an atrial event and ends with the sensed R-wave, and using the AR interval thus measured as the determined natural conduction time; and; if an R-wave is not sensed, using the duration of a previously measured AR interval of an immediately-preceding cardiac cycle during which an R-wave was sensed as the determined natural conduction time.

9. The method of claim 8, further including measuring the duration of the AR interval of an immediately preceding cardiac cycle during which an R-wave was sensed as the determined natural conduction time only when x consecutive cardiac cycles have elapsed without sensing an R-wave, where x is an integer between 4 and 512.

10. The method of claim 6, comprising generating and delivering the V-pulse at a delivery time within the cardiac cycle that is a prescribed amount Δ less than the natural conduction time determined in step (b).

11. The method of claim 6, wherein the pacemaker further includes means for defining a VA interval and means for generating an atrial stimulation pulse (A-pulse) at the conclusion of the VA interval, wherein the VA interval begins upon the occurrence of a ventricular event and terminates upon the occurrence of an atrial event, and wherein the method also includes: changing the VA interval by an appropriate amount so that the duration between successive A-pulses, comprising an A-to-A interval made up of the interval between an atrial event and the generation of the V-pulse as determined in step (c) plus the VA interval, remains unchanged.

12. The method of claim 11, wherein the appropriate amount by which the VA interval is changed comprises 1 to 100 msec.

13. The method of claim 6 wherein the step of determining the natural conduction time comprises measuring the natural conduction time for at least y cardiac cycles, where y is an integer, and computing an average of the natural conduction time measurements thus made, and using such average natural conduction time as the determined natural conduction time.

14. A dual-chamber pacemaker for controlling ventricular pacing as a function of a natural conduction time of a patient's heart, comprising:

an atrial channel comprising means for sensing a natural atrial depolarization (P-wave) and means for generating an atrial stimulation pulse (A-pulse) and delivering the A-pulse to an atrium of the patient's heart;

a ventricular channel comprising means for sensing a natural ventricular depolarization (R-wave) and means for generating a ventricular stimulation pulse (V-pulse) and delivering the V-pulse to a ventricle of the patient's heart at the conclusion of an AV interval unless an R-wave is sensed during the AV interval;

means for sensing a natural conduction time interval of the patient's heart through the atrial and ventricular channels, the natural conduction time interval comprising the time interval within a given cardiac cycle that commences with atrial activity, where atrial activity comprises either a sensed P-wave or a paced A-pulse, whichever occurs first within the given cardiac cycle, and that terminates upon a sensed R-wave; and timing means for defining the AV interval so that the AV interval commences with atrial activity and terminates at a time within the cardiac cycle that is a function of the natural conduction time.

15. The dual-chamber pacemaker of claim 14, wherein the timing means includes means for defining said AV interval to be equal to the natural conduction time interval ±Δ, where Δ is a specified amount.

16. The dual-chamber pacemaker of claim 15, wherein said timing means further includes:

means for defining a VA time interval that commences with a V-pulse and terminates with atrial activity, and wherein the AV interval plus the VA interval defines a pacing interval for the pacemaker; and means for altering the VA time interval by an appropriate amount so that the pacing interval remains unchanged.

* * * * *